United States Patent
Friedman et al.

(10) Patent No.: US 8,268,548 B2
(45) Date of Patent: Sep. 18, 2012

(54) MAP3KS AS MODIFIERS OF THE P53 PATHWAY AND METHODS OF USE

(75) Inventors: Lori Friedman, San Carlos, CA (US); Gregory D. Plowman, San Carlos, CA (US); Marcia Belvin, Albany, CA (US); Helen Francis-Lang, San Francisco, CA (US); Danix Li, Zionsville, IN (US); Roel P. Funke, Brisbane, CA (US)

(73) Assignee: Exelixis, Inc., South San Francisco, CA (US)

( * ) Notice: Subject to any disclaimer, the term of this patent is extended or adjusted under 35 U.S.C. 154(b) by 407 days.

(21) Appl. No.: 11/788,379

(22) Filed: Apr. 18, 2007

(65) Prior Publication Data

US 2009/0068186 A1    Mar. 12, 2009

Related U.S. Application Data

(63) Continuation of application No. 10/479,871, filed as application No. PCT/US02/17457 on Jun. 3, 2002, now abandoned.

(60) Provisional application No. 60/361,196, filed on Mar. 1, 2002, provisional application No. 60/357,253, filed on Feb. 15, 2002, provisional application No. 60/328,605, filed on Oct. 10, 2001, provisional application No. 60/296,076, filed on Jun. 5, 2001.

(51) Int. Cl.
*C12Q 1/68* (2006.01)

(52) U.S. Cl. .......................................... 435/6

(58) Field of Classification Search .................. None
See application file for complete search history.

(56) References Cited

U.S. PATENT DOCUMENTS 5,676,945 A   10/1997 Reddy
5,854,003 A   12/1998 Rothe et al.

FOREIGN PATENT DOCUMENTS

| WO | WO 94/24159 A1 | 10/1994 |
|---|---|---|
| WO | WO 99/41385 | * 8/1999 |
| WO | WO 99/41385 A1 | 8/1999 |
| WO | WO 99/47686 A2 | 9/1999 |
| WO | WO 00/55178 A1 | 9/2000 |
| WO | WO 02/14355 A2 | 2/2002 |
| WO | WO 03/091419 A2 | 6/2003 |

OTHER PUBLICATIONS

Fuchs et al (PNAS, Sep. 1998, 95: 10541-10546).*
Reddy, U.R. et al.: Homo sapiens mitogen-activated protein kinase kinase kinase 12 (MAP3K12), mRNA; Nov. 1, 2000; GI:5454183.
Homo sapiens mitogen-activated protein kinase kinase kinase 13 (MAP3K13), mRNA; Oct. 16, 2001; GI:13645287.
Sakuma H. et al.: Homo sapiens mitogen-activated protein kinase kinase kinase 13 (MAP3K13), mRNA; Nov. 1, 2000; GI:4758695.
Reddy U.R. et al.: Mitogen-activated protein kinase kinase kinase 12; zipper (leucine) protein kinase (Homo sapiens); Nov. 1, 2000; GI:5454184.
Sakuma H. et al.: Homo sapiens mitogen-activated protein kinase kinase kinase 13: leucine zipper-bearing (Homo sapiens); Jul. 12, 2002; GI:4758696.
Ellinger-Ziegelbauer et al., Molecular and Cellular Biology; May 1999; 19(5): 3857-3868.
Fuchs et al., PNAS, 1998, 95:10541-10546.
Ollman M. et al. , Cell, 2000, 101: 91-101.
Burgess et al., J. Cell Biol. 111:2129-2138, 1990.
Lazar et al., Mol. Cell Biol. 8:1247-1252, 1998.
Lee et al., "Sustained activation of Ras/Raf/mitogen-activated protein kinase cascade by the tumor suppressor p53," PNAS, 97:8302-8305 (Jul. 2000) XP002306483 ISSN: 0027-8424.
Agarwal et al., "Regulation of p53 expression by the RAS-MAP kinase Pathway," Oncogene, 20:2527-2536 (May 2001), XP0021306482 ISSN:0950-9232.
Tassan et al. Biology of the Cell, 2004, 96:193-199.
Schumacher et al. (Current Biology, 2001, 11:1722-1727, IDS).
Bowie et al. (Science, 1990, 247:1306-1310, IDS).

* cited by examiner

*Primary Examiner* — Sean E Aeder
(74) *Attorney, Agent, or Firm* — McDonnell Boehnen Hulbert & Berghoff LLP

(57) ABSTRACT

Human MAP3K genes are identified as modulators of the p53 pathway, and thus are therapeutic targets for disorders associated with defective p53 function. Methods for identifying modulators of p53, comprising screening for agents that modulate the activity of MAP3K are provided.

12 Claims, No Drawings

MAP3KS AS MODIFIERS OF THE P53 PATHWAY AND METHODS OF USE

REFERENCE TO RELATED APPLICATIONS

This application is a continuation of U.S. patent application Ser. No. 10/479,871, filed Mar. 21, 2005, which is a U.S. National Stage Application of PCT/US02/17457, filed Jun. 18, 2004, which claims priority to U.S. provisional application 60/479,781 filed Jun. 3, 2002, which claims the benefit of U.S. provisional patent applications 60/296,076 filed Jun. 5, 2001, 60/328,605 filed Oct. 10, 2001, 60/357,253 filed Feb. 15, 2002, and 60/361,196 filed Mar. 1, 2002. The contents of these applications are hereby incorporated by reference in their entireties.

BACKGROUND OF THE INVENTION

The p53 gene is mutated in over 50 different types of human cancers, including familial and spontaneous cancers, and is believed to be the most commonly mutated gene in human cancer (Zambetti and Levine, FASEB (1993) 7:855-865; Hollstein, et al., Nucleic Acids Res. (1994) 22:3551-3555). Greater than 90% of mutations in the p53 gene are missense mutations that alter a single amino acid that inactivates p53 function. Aberrant forms of human p53 are associated with poor prognosis, more aggressive tumors, metastasis, and short survival rates (Mitsudomi et al., Clin Cancer Res 2000 October; 6(10):4055-63; Koshland, Science (1993) 262:1953).

The human p53 protein normally functions as a central integrator of signals including DNA damage, hypoxia, nucleotide deprivation, and oncogene activation (Prives, Cell (1998) 95:5-8). In response to these signals, p53 protein levels are greatly increased with the result that the accumulated p53 activates cell cycle arrest or apoptosis depending on the nature and strength of these signals. Indeed, multiple lines of experimental evidence have pointed to a key role for p53 as a tumor suppressor (Levine, Cell (1997) 88:323-331). For example, homozygous p53 "knockout" mice are developmentally normal but exhibit nearly 100% incidence of neoplasia in the first year of life (Donehower et al., Nature (1992) 356:215-221).

The biochemical mechanisms and pathways through which p53 functions in normal and cancerous cells are not fully understood, but one clearly important aspect of p53 function is its activity as a gene-specific transcriptional activator. Among the genes with known p53-response elements are several with well-characterized roles in either regulation of the cell cycle or apoptosis, including GADD45, p21/Waf1/Cip1, cyclin G, Bax, IGF-BP3, and MDM2 (Levine, Cell (1997) 88:323-331).

Protein kinases (PKs) play a crucial role in regulating cellular processes, including growth factor response, cytoskeletal changes, gene expression, and metabolism. PKs have very similar sequences and can be grouped based on specificity for the acceptor amino acid. Most PKs phosphorylate either serine/threonine or tyrosine. However, some PKs, referred to as mixed-lineage kinases, have features of both serine/threonine and tyrosine PKs. All PKs have Src homology (SH) domains and can also be grouped as receptors or nonreceptors. Receptor PKs have a transmembrane region, an extracellular ligand-binding domain, and an intracellular catalytic domain.

Mitogen activated protein kinase kinase kinase 12 (MAP3K12), is a dual leucine zipper-bearing kinase, and a member of the mixed lineage protein kinase (MLK) (Reddy, U. and Pleasure, D., (1994) Biochem. Biophys. Res. Commun. 202: 613-620). MAP3K12 contains a COOH-terminal and NH2-terminal proline-rich domains suggestive of src homology 3 (SH3) domain binding regions, and can be autophosphorylated on serine and threonine residues (Holzman, L. et al., (1994) J. Biol. Chem. 269: 30808-30817). This kinase activates the SAPK/JNK signaling pathway, and may play a role in neuronal differentiation (Hirai, S., (1996) Oncogene 12: 641-650).

MAP3K13 protein, also called LZK (leucine zipper-bearing kinase) contains double leucine/isoleucine zippers, has no apparent signal sequence or transmembrane region but does contain a kinase catalytic domain, and an acidic domain at its C-terminal end (Sakuma, H. et al., (1997) J. Biol. Chem. 272: 28622-28629). MAP3K13 shares 86.4% amino acid identity with MAP3K12 and like MAP3K12 it is also a member of the mixed-lineage kinase family of proteins which contain similarities to both serine/threonine and tyrosine kinases (Sakuma, H. et al., (1997) J. Biol. Chem. 272: 28622-28629). These kinases activate the phosphorylation event of c-Jun and turn on JNK-1 (Sakuma, H. et al., (1997) J. Biol. Chem. 272: 28622-28629).

MAP3K12 and MAP3K13 are both highly conserved genes that have been found in organisms from yeast to man. MAP3K12 has been implicated in neuronal cell death (Xu, Z. et al. (2001) Mol Cell Biol 21:4713-24).

The ability to manipulate the genomes of model organisms such as *Drosophila* provides a powerful means to analyze biochemical processes that, due to significant evolutionary conservation, has direct relevance to more complex vertebrate organisms. Due to a high level of gene and pathway conservation, the strong similarity of cellular processes, and the functional conservation of genes between these model organisms and mammals, identification of the involvement of novel genes in particular pathways and their functions in such model organisms can directly contribute to the understanding of the correlative pathways and methods of modulating them in mammals (see, for example, Mechier B M et al., 1985 EMBO J 4:1551-1557; Gateff E. 1982 Adv. Cancer Res. 37: 33-74; Watson K L., et al., 1994 J Cell Sci. 18: 19-33; Miklos G L, and Rubin G M. 1996 Cell 86:521-529; Wassarman D A, et al., 1995 Curr Opin Gen Dev 5: 44-50; and Booth D R. 1999 Cancer Metastasis Rev. 18: 261-284). For example, a genetic screen can be carried out in an invertebrate model organism having underexpression (e.g. knockout) or overexpression of a gene (referred to as a "genetic entry point") that yields a visible phenotype. Additional genes are mutated in a random or targeted manner. When a gene mutation changes the original phenotype caused by the mutation in the genetic entry point, the gene is identified as a "modifier" involved in the same or overlapping pathway as the genetic entry point. When the genetic entry point is an ortholog of a human gene implicated in a disease pathway, such as p53, modifier genes can be identified that may be attractive candidate targets for novel therapeutics.

All references cited herein, including sequence information in referenced Genbank identifier numbers and website references, are incorporated herein in their entireties.

SUMMARY OF THE INVENTION

We have discovered genes that modify the p53 pathway in *Drosophila*, and identified their human orthologs, hereinafter referred to as MAP3Ks. The invention provides methods for utilizing these p53 modifier genes and polypeptides to identify candidate therapeutic agents that can be used in the treatment of disorders associated with defective p53 function.

Preferred MAP3K-modulating agents specifically bind to MAP3K polypeptides and restore p53 function. Other preferred MAP3K-modulating agents are nucleic acid modulators such as antisense oligomers and RNAi that repress MAP3K gene expression or product activity by, for example, binding to and inhibiting the respective nucleic acid (i.e. DNA or mRNA).

MAP3K-specific modulating agents may be evaluated by any convenient in vitro or in vivo assay for molecular interaction with a MAP3K polypeptide or nucleic acid. In one embodiment, candidate p53 modulating agents are tested with an assay system comprising a MAP3K polypeptide or nucleic acid. Candidate agents that produce a change in the activity of the assay system relative to controls are identified as candidate p53 modulating agents. The assay system may be cell-based or cell-free. MAP3K-modulating agents include MAP3K related proteins (e.g. dominant negative mutants, and biotherapeutics); MAP3K-specific antibodies; MAP3K-specific antisense oligomers and other nucleic acid modulators; and chemical agents that specifically bind MAP3K or compete with MAP3K binding target. In one specific embodiment, a small molecule modulator is identified using a kinase assay. In specific embodiments, the screening assay system is selected from a binding assay, an apoptosis assay, a cell proliferation assay, an angiogenesis assay, and a hypoxic induction assay.

In another embodiment, candidate p53 pathway modulating agents are further tested using a second assay system that detects changes in the p53 pathway, such as angiogenic, apoptotic, or cell proliferation changes produced by the originally identified candidate agent or an agent derived from the original agent. The second assay system may use cultured cells or non-human animals. In specific embodiments, the secondary assay system uses non-human animals, including animals predetermined to have a disease or disorder implicating the p53 pathway, such as an angiogenic, apoptotic, or cell proliferation disorder (e.g. cancer).

The invention further provides methods for modulating the p53 pathway in a mammalian cell by contacting the mammalian cell with an agent that specifically binds a MAP3K polypeptide or nucleic acid. The agent may be a small molecule modulator, a nucleic acid modulator, or an antibody and may be administered to a mammalian animal predetermined to have a pathology associated the p53 pathway.

DETAILED DESCRIPTION OF THE INVENTION

Genetic screens were designed to identify modifiers of the p53 pathway in and *Drosophila* in which p53 was overexpressed in the wing (Ollmann M, et al., Cell 2000 101: 91-101). The CG8789 gene was identified as a modifier of the p53 pathway. Accordingly, vertebrate orthologs of these modifiers, and preferably the human orthologs, MAP3K genes (i.e., nucleic acids and polypeptides) are attractive drug targets for the treatment of pathologies associated with a defective p53 signaling pathway, such as cancer.

In vitro and in vivo methods of assessing MAP3K function are provided herein. Modulation of the MAP3K or their respective binding partners is useful for understanding the association of the p53 pathway and its members in normal and disease conditions and for developing diagnostics and therapeutic modalities for p53 related pathologies. MAP3K-modulating agents that act by inhibiting or enhancing MAP3K expression, directly or indirectly, for example, by affecting a MAP3K function such as enzymatic (e.g., catalytic) or binding activity, can be identified using methods provided herein. MAP3K modulating agents are useful in diagnosis, therapy and pharmaceutical development.

Nucleic Acids and Polypeptides of the Invention

Sequences related to MAP3K nucleic acids and polypeptides that can be used in the invention are disclosed in Genbank (referenced by Genbank identifier (GI) number) as GI #s 5454183 (SEQ ID NO:1), 13645287 (SEQ ID NO:4), and 4758695 (SEQ ID NO:5) for nucleic acid, and GI #s 5454184 (SEQ ID NO:8) and 4758696 (SEQ ID NO:9) for polypeptides. Further, sequences of SEQ ID NOs: 2, 3, 6, and 7 can also be used in the invention.

MAP3Ks are kinase proteins with kinase domains. The term "MAP3K polypeptide" refers to a full-length MAP3K protein or a functionally active fragment or derivative thereof. A "functionally active" MAP3K fragment or derivative exhibits one or more functional activities associated with a full-length, wild-type MAP3K protein, such as antigenic or immunogenic activity, enzymatic activity, ability to bind natural cellular substrates, etc. The functional activity of MAP3K proteins, derivatives and fragments can be assayed by various methods known to one skilled in the art (Current Protocols in Protein Science (1998) Coligan et al., eds., John Wiley & Sons, Inc., Somerset, N.J.) and as further discussed below. For purposes herein, functionally active fragments also include those fragments that comprise one or more structural domains of a MAP3K, such as a kinase domain or a binding domain. Protein domains can be identified using the PFAM program (Bateman A., et al., Nucleic Acids Res, 1999, 27:260-2). For example, the kinase domain of MAP3K from GI # 5454184 (SEQ ID NO:8) is located at approximately amino acid residues 125-366 (PFAM 00069). Likewise, the kinase domain of MAP3K from GU 4758696 (SEQ ID NO:9) is located at approximately amino acid residues 168-409. Methods for obtaining MAP3K polypeptides are also further described below. In some embodiments, preferred fragments are functionally active, domain-containing fragments comprising at least 25 contiguous amino acids, preferably at least 50, more preferably 75, and most preferably at least 100 contiguous amino acids of any one of SEQ ID NOs:8 or 9 (a MAP3K). In further preferred embodiments, the fragment comprises the entire kinase (functionally active) domain.

The term "MAP3K nucleic acid" refers to a DNA or RNA molecule that encodes a MAP3K polypeptide. Preferably, the MAP3K polypeptide or nucleic acid or fragment thereof is from a human, but can also be an ortholog, or derivative thereof with at least 70% sequence identity, preferably at least 80%, more preferably 85%, still more preferably 90%, and most preferably at least 95% sequence identity with MAP3K. Normally, orthologs in different species retain the same function, due to presence of one or more protein motifs and/or 3-dimensional structures. Orthologs are generally identified by sequence homology analysis, such as BLAST analysis, usually using protein bait sequences. Sequences are assigned as a potential ortholog if the best hit sequence from the forward BLAST result retrieves the original query sequence in the reverse BLAST (Huynen M A and Bork P, Proc Natl Acad Sci (1998) 95:5849-5856; Huynen M A et al., Genome Research (2000) 10:1204-1210). Programs for multiple sequence alignment, such as CLUSTAL (Thompson J D et al, 1994, Nucleic Acids Res 22:4673-4680) may be used to highlight conserved regions and/or residues of orthologous proteins and to generate phylogenetic trees. In a phylogenetic tree representing multiple homologous sequences from diverse species (e.g., retrieved through BLAST analysis), orthologous sequences from two species generally appear closest on the tree with respect to all other sequences from these two species. Structural threading or other analysis of protein folding (e.g., using software by ProCeryon, Biosciences, Salzburg, Austria) may also identify potential orthologs. In evolution, when a gene duplication event follows speciation, a single gene in one species, such as *Drosophila*, may correspond to multiple genes (paralogs) in another, such as human. As used herein, the term "orthologs" encompasses paralogs. As used herein, "percent (%) sequence identity" with respect to a subject sequence, or a specified portion of a subject sequence, is defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403-410) with all the search parameters set to default values. The HSP S and HSP S2 parameters are dynamic values and are established by the program itself depending upon the composition of the particular sequence and composition of the particular database against which the sequence of interest is being searched. A % identity value is determined by the number of matching identical nucleotides or amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation.

A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids are arginine, lysine and histidine; interchangeable acidic amino acids are aspartic acid and glutamic acid; and interchangeable small amino acids are alanine, serine, threonine, cysteine and glycine.

Alternatively, an alignment for nucleic acid sequences is provided by the local homology algorithm of Smith and Waterman (Smith and Waterman, 1981, Advances in Applied Mathematics 2:482-489; database: European Bioinformatics Institute; Smith and Waterman, 1981, J. of Molec. Biol., 147:195-197; Nicholas et al., 1998, "A Tutorial on Searching Sequence Databases and Sequence Scoring Methods" and references cited therein.; W. R. Pearson, 1991, Genomics 11:635-650). This algorithm can be applied to amino acid sequences by using the scoring matrix developed by Dayhoff (Dayhoff: Atlas of Protein Sequences and Structure, M. 0. Dayhoff ed., 5 suppl. 3:353-358, National Biomedical Research Foundation, Washington, D.C., USA), and normalized by Gribskov (Gribskov 1986 Nucl. Acids Res. 14(6): 6745-6763). The Smith-Waterman algorithm may be employed where default parameters are used for scoring (for example, gap open penalty of 12, gap extension penalty of two). From the data generated, the "Match" value reflects "sequence identity."

Derivative nucleic acid molecules of the subject nucleic acid molecules include sequences that hybridize to the nucleic acid sequence of any of SEQ ID NOs: 1, 2, 3, 4, 5, 6, or 7 The stringency of hybridization can be controlled by temperature, ionic strength, pH, and the presence of denaturing agents such as formamide during hybridization and washing. Conditions routinely used are set out in readily available procedure texts (e.g., Current Protocol in Molecular Biology, Vol. 1, Chap. 2.10, John Wiley & Sons, Publishers (1994); Sambrook et al., Molecular Cloning, Cold Spring Harbor (1989)). In some embodiments, a nucleic acid molecule of the invention is capable of hybridizing to a nucleic acid molecule containing the nucleotide sequence of any one of SEQ ID NOs: 1, 2, 3, 4, 5, 6, or 7 under stringent hybridization conditions that comprise: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 µg/ml herring sperm DNA; hybridization for 18-20 hours at 65° C. in a solution containing 6×SSC, 1×Denhardt's solution, 100 µg/ml yeast tRNA and 0.05% sodium pyrophosphate; and washing of filters at 65° C. for 1 h in a solution containing 0.2×SSC and 0.1% SDS (sodium dodecyl sulfate).

In other embodiments, moderately stringent hybridization conditions are used that comprise: pretreatment of filters containing nucleic acid for 6 h at 40° C. in a solution containing 35% formamide, 5×SSC, 50 mM Tris-HCl (pH7.5), 5 mM EDTA, 0.1% PVP, 0.1% FICOLL®, 1% BSA, and 500 µg/ml denatured salmon sperm DNA; hybridization for 18-20 h at 40° C. in a solution containing 35% formamide, 5×SSC, 50 mM Tris-HCl (pH7.5), 5 mM EDTA, 0.02% PVP, 0.02% FICOLL®, 0.2% BSA, 100 µg/ml salmon sperm DNA, and 10% (wt/vol) dextran sulfate; followed by washing twice for 1 hour at 55° C. in a solution containing 2×SSC and 0.1% SDS.

Alternatively, low stringency conditions can be used that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 µg/ml denatured sheared salmon sperm DNA; hybridization in the same buffer for 18 to 20 hours; and washing of filters in 1×SSC at about 37° C. for 1 hour.

Isolation, Production, Expression, and Mis-Expression of MAP3K Nucleic Acids and Polypeptides MAP3K nucleic acids and polypeptides, useful for identifying and testing agents that modulate MAP3K function and for other applications related to the involvement of MAP3K in the p53 pathway. MAP3K nucleic acids and derivatives and orthologs thereof may be obtained using any available method. For instance, techniques for isolating cDNA or genomic DNA sequences of interest by screening DNA libraries or by using polymerase chain reaction (PCR) are well known in the art. In general, the particular use for the protein will dictate the particulars of expression, production, and purification methods. For instance, production of proteins for use in screening for modulating agents may require methods that preserve specific biological activities of these proteins, whereas production of proteins for antibody generation may require structural integrity of particular epitopes. Expression of proteins to be purified for screening or antibody production may require the addition of specific tags (e.g., generation of fusion proteins). Overexpression of a MAP3K protein for assays used to assess MAP3K function, such as involvement in cell cycle regulation or hypoxic response, may require expression in eukaryotic cell lines capable of these cellular activities. Techniques for the expression, production, and purification of proteins are well known in the art; any suitable means therefore may be used (e.g., Higgins S J and Hames B D (eds.) Protein Expression: A Practical Approach, Oxford University Press Inc., New York 1999; Stanbury P F et al., Principles of Fermentation Technology, $2^{nd}$ edition, Elsevier Science, New York, 1995; Doonan S (ed.) Protein Purification Protocols, Humana Press, New Jersey, 1996; Coligan J E et al, Current Protocols in Protein Science (eds.), 1999, John Wiley & Sons, New York). In particular embodiments, recombinant MAP3K is expressed in a cell line known to have defective p53 function (e.g. SAOS-2 osteoblasts, H11299 lung cancer cells, C33A and HT3 cervical cancer cells, HT-29 and DLD-1 colon cancer cells, among others, available from American Type Culture Collection (ATCC), Manassas, Va.). The recombinant cells are used in cell-based screening assay systems of the invention, as described further below.

The nucleotide sequence encoding a MAP3K polypeptide can be inserted into any appropriate expression vector. The necessary transcriptional and translational signals, including promoter/enhancer element, can derive from the native MAP3K gene and/or its flanking regions or can be heterologous. A variety of host-vector expression systems may be utilized, such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, plasmid, or cosmid DNA. A host cell strain that modulates the expression of, modifies, and/or specifically processes the gene product may be used.

To detect expression of the MAP3K gene product, the expression vector can comprise a promoter operably linked to a MAP3K gene nucleic acid, one or more origins of replication, and, one or more selectable markers (e.g. thymidine kinase activity, resistance to antibiotics, etc.). Alternatively, recombinant expression vectors can be identified by assaying for the expression of the MAP3K gene product based on the physical or functional properties of the MAP3K protein in in vitro assay systems (e.g. immunoassays).

The MAP3K protein, fragment, or derivative may be optionally expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. A chimeric product may also be made by protein synthetic techniques, e.g. by use of a peptide synthesizer (Hunkapiller et al., Nature (1984) 310:105-111).

Once a recombinant cell that expresses the MAP3K gene sequence is identified, the gene product can be isolated and purified using standard methods (e.g. ion exchange, affinity, and gel exclusion chromatography; centrifugation; differential solubility; electrophoresis, cite purification reference). Alternatively, native MAP3K proteins can be purified from natural sources, by standard methods (e.g. immunoaffinity purification). Once a protein is obtained, it may be quantified and its activity measured by appropriate methods, such as immunoassay, bioassay, or other measurements of physical properties, such as crystallography.

The methods of this invention may also use cells that have been engineered for altered expression (mis-expression) of MAP3K or other genes associated with the p53 pathway. As used herein, mis-expression encompasses ectopic expression, over-expression, under-expression, and non-expression (e.g. by gene knock-out or blocking expression that would otherwise normally occur).

Genetically Modified Animals

Animal models that have been genetically modified to alter MAP3K expression may be used in in vivo assays to test for activity of a candidate p53 modulating agent, or to further assess the role of MAP3K in a p53 pathway process such as apoptosis or cell proliferation. Preferably, the altered MAP3K expression results in a detectable phenotype, such as decreased or increased levels of cell proliferation, angiogenesis, or apoptosis compared to control animals having normal MAP3K expression. The genetically modified animal may additionally have altered p53 expression (e.g. p53 knockout). Preferred genetically modified animals are mammals such as primates, rodents (preferably mice), cows, horses, goats, sheep, pigs, dogs and cats. Preferred non-mammalian species include zebrafish, C. elegans, and Drosophila. Preferred genetically modified animals are transgenic animals having a heterologous nucleic acid sequence present as an extrachromosomal element in a portion of its cells, i.e. mosaic animals (see, for example, techniques described by Jakobovits, 1994, Curr. Biol. 4:761-763.) or stably integrated into its germ line DNA (i.e., in the genomic sequence of most or all of its cells). Heterologous nucleic acid is introduced into the germ line of such transgenic animals by genetic manipulation of, for example, embryos or embryonic stem cells of the host animal.

Methods of making transgenic animals are well-known in the art (for transgenic mice see Brinster et al., Proc. Nat. Acad. Sci. USA 82: 4438-4442 (1985), U.S. Pat. Nos. 4,736,866 and 4,870,009, both by Leder et al., U.S. Pat. No. 4,873,191 by Wagner et al., and Hogan, B., Manipulating the Mouse Embryo, Cold Spring Harbor Laboratory Press, Cold Spring Harbor, N.Y., (1986); for particle bombardment see U.S. Pat. No. 4,945,050, by Sandford et al.; for transgenic Drosophila see Rubin and Spradling, Science (1982) 218:348-53 and U.S. Pat. No. 4,670,388; for transgenic insects see Berghammer A. J. et al., A Universal Marker for Transgenic Insects (1999) Nature 402:370-371; for transgenic Zebrafish see Lin S., Transgenic Zebrafish, Methods Mol Biol. (2000); 136: 375-3830); for microinjection procedures for fish, amphibian eggs and birds see Houdebine and Chourrout, Experientia (1991) 47:897-905; for transgenic rats see Hammer et al., Cell (1990) 63:1099-1112; and for culturing of embryonic stem (ES) cells and the subsequent production of transgenic animals by the introduction of DNA into ES cells using methods such as electroporation, calcium phosphate/DNA precipitation and direct injection see, e.g., Teratocarcinomas and Embryonic Stem Cells, A Practical Approach, E. J. Robertson, ed., IRL Press (1987)). Clones of the nonhuman transgenic animals can be produced according to available methods (see Wilmut, I. et al. (1997) Nature 385:810-813; and PCT International Publication Nos. WO 97/07668 and WO 97/07669).

In one embodiment, the transgenic animal is a "knock-out" animal having a heterozygous or homozygous alteration in the sequence of an endogenous MAP3K gene that results in a decrease of MAP3K function, preferably such that MAP3K expression is undetectable or insignificant. Knock-out animals are typically generated by homologous recombination with a vector comprising a transgene having at least a portion of the gene to be knocked out. Typically a deletion, addition or substitution has been introduced into the transgene to functionally disrupt it. The transgene can be a human gene (e.g., from a human genomic clone) but more preferably is an ortholog of the human gene derived from the transgenic host species. For example, a mouse MAP3K gene is used to construct a homologous recombination vector suitable for altering an endogenous MAP3K gene in the mouse genome. Detailed methodologies for homologous recombination in mice are available (see Capecchi, Science (1989) 244:1288-1292; Joyner et al., Nature (1989) 338:153-156). Procedures for the production of non-rodent transgenic mammals and other animals are also available (Houdebine and Chourrout, supra; Pursel et al., Science (1989) 244:1281-1288; Simms et al., Bio/Technology (1988) 6:179-183). In a preferred embodiment, knock-out animals, such as mice harboring a knockout of a specific gene, may be used to produce antibodies against the human counterpart of the gene that has been knocked out (Claesson M H et al., (1994) Scan J Immunol 40:257-264; Declerck P J et al., (1995) J Biol Chem. 270: 8397-400).

In another embodiment, the transgenic animal is a "knock-in" animal having an alteration in its genome that results in altered expression (e.g., increased (including ectopic) or decreased expression) of the MAP3K gene, e.g., by introduction of additional copies of MAP3K, or by operatively inserting a regulatory sequence that provides for altered expression of an endogenous copy of the MAP3K gene. Such regulatory sequences include inducible, tissue-specific, and constitutive promoters and enhancer elements. The knock-in can be homozygous or heterozygous.

Transgenic nonhuman animals can also be produced that contain selected systems allowing for regulated expression of the transgene. One example of such a system that may be produced is the cre/loxP recombinase system of bacteriophage PI (Lakso et al., PNAS (1992) 89:6232-6236; U.S. Pat. No. 4,959,317). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase. Another example of a recombinase system is the FLP recombinase system of Saccharomyces cerevisiae (O'Gorman et al. (1991) Science 251:1351-1355; U.S. Pat. No. 5,654,182). In a preferred embodiment, both Cre-LoxP and Flp-Frt are used in the same system to regulate expression of the transgene, and for sequential deletion of vector sequences in the same cell (Sun X et al (2000) Nat Genet 25:83-6).

The genetically modified animals can be used in genetic studies to further elucidate the p53 pathway, as animal models of disease and disorders implicating defective p53 function, and for in vivo testing of candidate therapeutic agents, such as those identified in screens described below. The candidate therapeutic agents are administered to a genetically modified animal having altered MAP3K function and phenotypic changes are compared with appropriate control animals such as genetically modified animals that receive placebo treatment, and/or animals with unaltered MAP3K expression that receive candidate therapeutic agent.

In addition to the above-described genetically modified animals having altered MAP3K function, animal models having defective p53 function (and otherwise normal MAP3K function), can be used in the methods of the present invention. For example, a p53 knockout mouse can be used to assess, in vivo, the activity of a candidate p53 modulating agent identified in one of the in vitro assays described below. p53 knockout mice are described in the literature (Jacks et al., Nature 2001; 410:1111-1116, 1043-1044; Donehower et al., supra). Preferably, the candidate p53 modulating agent when administered to a model system with cells defective in p53 function, produces a detectable phenotypic change in the model system indicating that the p53 function is restored, i.e., the cells exhibit normal cell cycle progression.

Modulating Agents

The invention provides methods to identify agents that interact with and/or modulate the function of MAP3K and/or the p53 pathway. Such agents are useful in a variety of diagnostic and therapeutic applications associated with the p53 pathway, as well as in further analysis of the MAP3K protein and its contribution to the p53 pathway. Accordingly, the invention also provides methods for modulating the p53 pathway comprising the step of specifically modulating MAP3K activity by administering a MAP3K-interacting or -modulating agent.

In a preferred embodiment, MAP3K-modulating agents inhibit or enhance MAP3K activity or otherwise affect normal MAP3K function, including transcription, protein expression, protein localization, and cellular or extra-cellular activity. In a further preferred embodiment, the candidate p53 pathway-modulating agent specifically modulates the function of the MAP3K. The phrases "specific modulating agent", "specifically modulates", etc., are used herein to refer to modulating agents that directly bind to the MAP3K polypeptide or nucleic acid, and preferably inhibit, enhance, or otherwise alter, the function of the MAP3K. The term also encompasses modulating agents that alter the interaction of the MAP3K with a binding partner or substrate (e.g. by binding to a binding partner of a MAP3K, or to a protein/binding partner complex, and inhibiting function).

Preferred MAP3K-modulating agents include small molecule compounds; MAP3K-interacting proteins, including antibodies and other biotherapeutics; and nucleic acid modulators such as antisense and RNA inhibitors. The modulating agents may be formulated in pharmaceutical compositions, for example, as compositions that may comprise other active ingredients, as in combination therapy, and/or suitable carriers or excipients. Techniques for formulation and administration of the compounds may be found in "Remington's Pharmaceutical Sciences" Mack Publishing Co., Easton, Pa., $19^{th}$ edition.

Small Molecule Modulators

Small molecules, are often preferred to modulate function of proteins with enzymatic function, and/or containing protein interaction domains. Chemical agents, referred to in the art as "small molecule" compounds are typically organic, non-peptide molecules, having a molecular weight less than 10,000, preferably less than 5,000, more preferably less than 1,000, and most preferably less than 500. This class of modulators includes chemically synthesized molecules, for instance, compounds from combinatorial chemical libraries. Synthetic compounds may be rationally designed or identified based on known or inferred properties of the MAP3K protein or may be identified by screening compound libraries. Alternative appropriate modulators of this class are natural products, particularly secondary metabolites from organisms such as plants or fungi, which can also be identified by screening compound libraries for MAP3K-modulating activity. Methods for generating and obtaining compounds are well known in the art (Schreiber S L, Science (2000) 151: 1964-1969; Radmann J and Gunther J, Science (2000) 151:1947-1948).

Small molecule modulators identified from screening assays, as described below, can be used as lead compounds from which candidate clinical compounds may be designed, optimized, and synthesized. Such clinical compounds may have utility in treating pathologies associated with the p53 pathway. The activity of candidate small molecule modulating agents may be improved several-fold through iterative secondary functional validation, as further described below, structure determination, and candidate modulator modification and testing. Additionally, candidate clinical compounds are generated with specific regard to clinical and pharmacological properties. For example, the reagents may be derivatized and re-screened using in vitro and in vivo assays to optimize activity and minimize toxicity for pharmaceutical development.

Protein Modulators

Specific MAP3K-interacting proteins are useful in a variety of diagnostic and therapeutic applications related to the p53 pathway and related disorders, as well as in validation assays for other MAP3K-modulating agents. In a preferred embodiment, MAP3K-interacting proteins affect normal MAP3K function, including transcription, protein expression, protein localization, and cellular or extra-cellular activity. In another embodiment, MAP3K-interacting proteins are useful in detecting and providing information about the function of MAP3K proteins, as is relevant to p53 related disorders, such as cancer (e.g., for diagnostic means).

An MAP3K-interacting protein may be endogenous, i.e. one that naturally interacts genetically or biochemically with a MAP3K, such as a member of the MAP3K pathway that modulates MAP3K expression, localization, and/or activity. MAP3K-modulators include dominant negative forms of MAP3K-interacting proteins and of MAP3K proteins themselves. Yeast two-hybrid and variant screens offer preferred methods for identifying endogenous MAP3K-interacting proteins (Finley, R. L. et al. (1996) in DNA Cloning-Expression Systems: A Practical Approach, eds. Glover D. & Hames B. D (Oxford University Press, Oxford, England), pp. 169-203; Fashema S F et al., Gene (2000) 250:1-14; Drees B L Curr Opin Chem Biol (1999) 3:64-70; Vidal M and Legrain P Nucleic Acids Res (1999) 27:919-29; and U.S. Pat. No. 5,928,868). Mass spectrometry is an alternative preferred method for the elucidation of protein complexes (reviewed in, e.g., Pandley A and Mann M, Nature (2000) 405:837-846; Yates J R $3^{rd}$, Trends Genet (2000) 16:5-8).

An MAP3K-interacting protein may be an exogenous protein, such as a MAP3K-specific antibody or a T-cell antigen receptor (see, e.g., Harlow and Lane (1988) Antibodies, A Laboratory Manual, Cold Spring Harbor Laboratory; Harlow and Lane (1999) Using antibodies: a laboratory manual. Cold Spring Harbor, N.Y.: Cold Spring Harbor Laboratory Press). MAP3K antibodies are further discussed below.

In preferred embodiments, a MAP3K-interacting protein specifically binds a MAP3K protein. In alternative preferred embodiments, a MAP3K-modulating agent binds a MAP3K substrate, binding partner, or cofactor.

Antibodies

In another embodiment, the protein modulator is a MAP3K specific antibody agonist or antagonist. The antibodies have therapeutic and diagnostic utilities, and can be used in screening assays to identify MAP3K modulators. The antibodies can also be used in dissecting the portions of the MAP3K pathway responsible for various cellular responses and in the general processing and maturation of the MAP3K.

Antibodies that specifically bind MAP3K polypeptides can be generated using known methods. Preferably the antibody is specific to a mammalian ortholog of MAP3K polypeptide, and more preferably, to human MAP3K. Antibodies may be polyclonal, monoclonal (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Epitopes of MAP3K which are particularly antigenic can be selected, for example, by routine screening of MAP3K polypeptides for antigenicity or by applying a theoretical method for selecting antigenic regions of a protein (Hopp and Wood (1981), Proc. Natl. Acad. Sci. U.S.A. 78:3824-28; Hopp and Wood, (1983) Mol. Immunol. 20:483-89; Sutcliffe et al., (1983) Science 219:660-66) to the amino acid sequence shown in any of SEQ ID NOs:8 or 9. Monoclonal antibodies with affinities of $10^8$ M$^{-1}$ preferably $10^9$ M$^{-1}$ to $10^{10}$ M$^{-1}$, or stronger can be made by standard procedures as described (Harlow and Lane, supra; Goding (1986) Monoclonal Antibodies: Principles and Practice (2d ed) Academic Press, New York; and U.S. Pat. Nos. 4,381,292; 4,451,570; and 4,618,577). Antibodies may be generated against crude cell extracts of MAP3K or substantially purified fragments thereof. If MAP3K fragments are used, they preferably comprise at least 10, and more preferably, at least 20 contiguous amino acids of a MAP3K protein. In a particular embodiment, MAP3K-specific antigens and/or immunogens are coupled to carrier proteins that stimulate the immune response. For example, the subject polypeptides are covalently coupled to the keyhole limpet hemocyanin (KLH) carrier, and the conjugate is emulsified in Freund's complete adjuvant, which enhances the immune response. An appropriate immune system such as a laboratory rabbit or mouse is immunized according to conventional protocols.

The presence of MAP3K-specific antibodies is assayed by an appropriate assay such as a solid phase enzyme-linked immunosorbant assay (ELISA) using immobilized corresponding MAP3K polypeptides. Other assays, such as radioimmunoassays or fluorescent assays might also be used.

Chimeric antibodies specific to MAP3K polypeptides can be made that contain different portions from different animal species. For instance, a human immunoglobulin constant region may be linked to a variable region of a murine mAb, such that the antibody derives its biological activity from the human antibody, and its binding specificity from the murine fragment. Chimeric antibodies are produced by splicing together genes that encode the appropriate regions from each species (Morrison et al., Proc. Natl. Acad. Sci. (1984) 81:6851-6855; Neuberger et al., Nature (1984) 312:604-608; Takeda et al., Nature (1985) 31:452-454). Humanized antibodies, which are a form of chimeric antibodies, can be generated by grafting complementary-determining regions (CDRS) (Carlos, T. M., J. M. Harlan. 1994. Blood 84:2068-2101) of mouse antibodies into a background of human framework regions and constant regions by recombinant DNA technology (Riechmann LM, et al., 1988 Nature 323:323-327). Humanized antibodies contain ~10% murine sequences and ~90% human sequences, and thus further reduce or eliminate immunogenicity, while retaining the antibody specificities (Co M S, and Queen C. 1991 Nature 351:501-501; Morrison S L. 1992 Ann. Rev. Immun. 10:239-265). Humanized antibodies and methods of their production are well-known in the art (U.S. Pat. Nos. 5,530,101, 5,585,089, 5,693,762, and 6,180,370).

MAP3K-specific single chain antibodies which are recombinant, single chain polypeptides formed by linking the heavy and light chain fragments of the Fv regions via an amino acid bridge, can be produced by methods known in the art (U.S. Pat. No. 4,946,778; Bird, Science (1988) 242:423-426; Huston et al., Proc. Natl. Acad. Sci. USA (1988) 85:5879-5883; and Ward et al., Nature (1989) 334:544-546).

Other suitable techniques for antibody production involve in vitro exposure of lymphocytes to the antigenic polypeptides or alternatively to selection of libraries of antibodies in phage or similar vectors (Huse et al., Science (1989) 246:1275-1281). As used herein, T-cell antigen receptors are included within the scope of antibody modulators (Harlow and Lane, 1988, supra).

The polypeptides and antibodies of the present invention may be used with or without modification. Frequently, antibodies will be labeled by joining, either covalently or non-covalently, a substance that provides for a detectable signal, or that is toxic to cells that express the targeted protein (Menard S, et al., Int J. Biol Markers (1989) 4:131-134). A wide variety of labels and conjugation techniques are known and are reported extensively in both the scientific and patent literature. Suitable labels include radionuclides, enzymes, substrates, cofactors, inhibitors, fluorescent moieties, fluorescent emitting lanthanide metals, chemiluminescent moieties, bioluminescent moieties, magnetic particles, and the like (U.S. Pat. Nos. 3,817,837; 3,850,752; 3,939,350; 3,996,345; 4,277,437; 4,275,149; and 4,366,241). Also, recombinant immunoglobulins may be produced (U.S. Pat. No. 4,816,567). Antibodies to cytoplasmic polypeptides may be delivered and reach their targets by conjugation with membrane-penetrating toxin proteins (U.S. Pat. No. 6,086,900).

When used therapeutically in a patient, the antibodies of the subject invention are typically administered parenterally, when possible at the target site, or intravenously. The therapeutically effective dose and dosage regimen is determined by clinical studies. Typically, the amount of antibody administered is in the range of about 0.1 mg/kg-to about 10 mg/kg of patient weight. For parenteral administration, the antibodies are formulated in a unit dosage injectable form (e.g., solution, suspension, emulsion) in association with a pharmaceutically acceptable vehicle. Such vehicles are inherently nontoxic and non-therapeutic. Examples are water, saline, Ringer's solution, dextrose solution, and 5% human serum albumin. Nonaqueous vehicles such as fixed oils, ethyl oleate, or liposome carriers may also be used. The vehicle may contain minor amounts of additives, such as buffers and preservatives, which enhance isotonicity and chemical stability or otherwise enhance therapeutic potential. The antibodies' concentrations in such vehicles are typically in the range of about 1 mg/ml to about 10 mg/ml. Immunotherapeutic methods are further described in the literature (U.S. Pat. No. 5,859,206; WO0073469).

Nucleic Acid Modulators

Other preferred MAP3K-modulating agents comprise nucleic acid molecules, such as antisense oligomers or double stranded RNA (dsRNA), which generally inhibit MAP3K activity. Preferred nucleic acid modulators interfere with the function of the MAP3K nucleic acid such as DNA replication, transcription, translocation of the MAP3K RNA to the site of protein translation, translation of protein from the MAP3K RNA, splicing of the MAP3K RNA to yield one or more mRNA species, or catalytic activity which may be engaged in or facilitated by the MAP3K RNA.

In one embodiment, the antisense oligomer is an oligonucleotide that is sufficiently complementary to a MAP3K mRNA to bind to and prevent translation, preferably by binding to the 5' untranslated region. MAP3K-specific antisense oligonucleotides, preferably range from at least 6 to about 200 nucleotides. In some embodiments the oligonucleotide is preferably at least 10, 15, or 20 nucleotides in length. In other embodiments, the oligonucleotide is preferably less than 50, 40, or 30 nucleotides in length. The oligonucleotide can be DNA or RNA or a chimeric mixture or derivatives or modified versions thereof, single-stranded or double-stranded. The oligonucleotide can be modified at the base moiety, sugar moiety, or phosphate backbone. The oligonucleotide may include other appending groups such as peptides, agents that facilitate transport across the cell membrane, hybridization-triggered cleavage agents, and intercalating agents.

In another embodiment, the antisense oligomer is a phosphothioate morpholino oligomer (PMO). PMOs are assembled from four different morpholino subunits, each of which contain one of four genetic bases (A, C, G, or T) linked to a six-membered morpholine ring. Polymers of these subunits are joined by non-ionic phosphordiamidate intersubunit linkages. Details of how to make and use PMOs and other antisense oligomers are well known in the art (e.g. see WO99/18193; Probst J C, Antisense Oligodeoxynucleotide and Ribozyme Design, Methods. (2000) 22(3):271-281; Summerton J, and Weller D. 1997 Antisense Nucleic Acid Drug Dev.: 7:187-95; U.S. Pat. No. 5,235,033; and U.S. Pat. No. 5,378,841).

Alternative preferred MAP3K nucleic acid modulators are double-stranded RNA species mediating RNA interference (RNAi). RNAi is the process of sequence-specific, post-transcriptional gene silencing in animals and plants, initiated by double-stranded RNA (dsRNA) that is homologous in sequence to the silenced gene. Methods relating to the use of RNAi to silence genes in *C. elegans, Drosophila*, plants, and humans are known in the art (Fire A, et al., 1998 Nature 391:806-811; Fire, A. Trends Genet. 15, 358-363 (1999); Sharp, P. A. RNA interference 2001. Genes Dev. 15, 485-490 (2001); Hammond, S. M., et al., Nature Rev. Genet. 2, 110-1119 (2001); Tuschl, T. Chem. Biochem. 2, 239-245 (2001); Hamilton, A. et al., Science 286, 950-952 (1999); Hammond, S. M., et al., Nature 404, 293-296 (2000); Zamore, P. D., et al., Cell 101, 25-33 (2000); Bernstein, E., et al., Nature 409, 363-366 (2001); Elbashir, S. M., et al., Genes Dev. 15, 188-200 (2001); WO0129058; WO9932619; Elbashir S M, et al., 2001 Nature 411:494-498).

Nucleic acid modulators are commonly used as research reagents, diagnostics, and therapeutics. For example, antisense oligonucleotides, which are able to inhibit gene expression with exquisite specificity, are often used to elucidate the function of particular genes (see, for example, U.S. Pat. No. 6,165,790). Nucleic acid modulators are also used, for example, to distinguish between functions of various members of a biological pathway. For example, antisense oligomers have been employed as therapeutic moieties in the treatment of disease states in animals and man and have been demonstrated in numerous clinical trials to be safe and effective (Milligan J F, et al, Current Concepts in Antisense Drug Design, J Med Chem. (1993) 36:1923-1937; Tonkinson J L et al., Antisense Oligodeoxynucleotides as Clinical Therapeutic Agents, Cancer Invest. (1996) 14:54-65). Accordingly, in one aspect of the invention, a MAP3K-specific nucleic acid modulator is used in an assay to further elucidate the role of the MAP3K in the p53 pathway, and/or its relationship to other members of the pathway. In another aspect of the invention, a MAP3K-specific antisense oligomer is used as a therapeutic agent for treatment of p53-related disease states.

Assay Systems

The invention provides assay systems and screening methods for identifying specific modulators of MAP3K activity. As used herein, an "assay system" encompasses all the components required for performing and analyzing results of an assay that detects and/or measures a particular event. In general, primary assays are used to identify or confirm a modulator's specific biochemical or molecular effect with respect to the MAP3K nucleic acid or protein. In general, secondary assays further assess the activity of a MAP3K modulating agent identified by a primary assay and may confirm that the modulating agent affects MAP3K in a manner relevant to the p53 pathway. In some cases, MAP3K modulators will be directly tested in a secondary assay.

In a preferred embodiment, the screening method comprises contacting a suitable assay system comprising a MAP3K polypeptide with a candidate agent under conditions whereby, but for the presence of the agent, the system provides a reference activity (e.g. kinase activity), which is based on the particular molecular event the screening method detects. A statistically significant difference between the agent-biased activity and the reference activity indicates that the candidate agent modulates MAP3K activity, and hence the p53 pathway.

Primary Assays

The type of modulator tested generally determines the type of primary assay.

Primary Assays for Small Molecule Modulators

For small molecule modulators, screening assays are used to identify candidate modulators. Screening assays may be cell-based or may use a cell-free system that recreates or retains the relevant biochemical reaction of the target protein (reviewed in Sittampalam G S et al., Curr Opin Chem Biol (1997) 1:384-91 and accompanying references). As used herein the term "cell-based" refers to assays using live cells, dead cells, or a particular cellular fraction, such as a membrane, endoplasmic reticulum, or mitochondrial fraction. The term "cell free" encompasses assays using substantially purified protein (either endogenous or recombinantly produced), partially purified or crude cellular extracts. Screening assays may detect a variety of molecular events, including protein-DNA interactions, protein-protein interactions (e.g., receptor-ligand binding), transcriptional activity (e.g., using a reporter gene), enzymatic activity (e.g., via a property of the substrate), activity of second messengers, immunogenicity and changes in cellular morphology or other cellular characteristics. Appropriate screening assays may use a wide range of detection methods including fluorescent, radioactive, colorimetric, spectrophotometric, and amperometric methods, to provide a read-out for the particular molecular event detected.

Cell-based screening assays usually require systems for recombinant expression of MAP3K and any auxiliary proteins demanded by the particular assay. Appropriate methods for generating recombinant proteins produce sufficient quantities of proteins that retain their relevant biological activities and are of sufficient purity to optimize activity and assure assay reproducibility. Yeast two-hybrid and variant screens, and mass spectrometry provide preferred methods for determining protein-protein interactions and elucidation of protein complexes. In certain applications, when MAP3K-interacting proteins are used in screens to identify small molecule modulators, the binding specificity of the interacting protein to the MAP3K protein may be assayed by various known methods such as substrate processing (e.g. ability of the candidate MAP3K-specific binding agents to function as negative effectors in MAP3K-expressing cells), binding equilibrium constants (usually at least about $10^7$ $M^{-1}$, preferably at least about $10^8$ $M^{-1}$, more preferably at least about $10^9$ $M^{-1}$), and immunogenicity (e.g. ability to elicit MAP3K specific antibody in a heterologous host such as a mouse, rat, goat or rabbit). For enzymes and receptors, binding may be assayed by, respectively, substrate and ligand processing.

The screening assay may measure a candidate agent's ability to specifically bind to or modulate activity of a MAP3K polypeptide, a fusion protein thereof, or to cells or membranes bearing the polypeptide or fusion protein. The MAP3K polypeptide can be full length or a fragment thereof that retains functional MAP3K activity. The MAP3K polypeptide may be fused to another polypeptide, such as a peptide tag for detection or anchoring, or to another tag. The MAP3K polypeptide is preferably human MAP3K, or is an ortholog or derivative thereof as described above. In a preferred embodiment, the screening assay detects candidate agent-based modulation of MAP3K interaction with a binding target, such as an endogenous or exogenous protein or other substrate that has MAP3K-specific binding activity, and can be used to assess normal MAP3K gene function.

Suitable assay formats that may be adapted to screen for MAP3K modulators are known in the art. Preferred screening assays are high throughput or ultra high throughput and thus provide automated, cost-effective means of screening compound libraries for lead compounds (Fernandes P B, Curr Opin Chem Biol (1998) 2:597-603; Sundberg S A, Curr Opin Biotechnol 2000, 11:47-53). In one preferred embodiment, screening assays uses fluorescence technologies, including fluorescence polarization, time-resolved fluorescence, and fluorescence resonance energy transfer. These systems offer means to monitor protein-protein or DNA-protein interactions in which the intensity of the signal emitted from dye-labeled molecules depends upon their interactions with partner molecules (e.g., Selvin P R, Nat Struct Biol (2000) 7:730-4; Fernandes P B, supra; Hertzberg R P and Pope A J, Curr Opin Chem Biol (2000) 4:445-451).

A variety of suitable assay systems may be used to identify candidate MAP3K and p53 pathway modulators (e.g. U.S. Pat. No. 6,165,992 (kinase assays); U.S. Pat. Nos. 5,550,019 and 6,133,437 (apoptosis assays); and U.S. Pat. No. 6,020,135 (p53 modulation), among others). Specific preferred assays are described in more detail below.

Kinase assays. In some preferred embodiments the screening assay detects the ability of the test agent to modulate the kinase activity of a MAP3K polypeptide. In further embodiments, a cell-free kinase assay system is used to identify a candidate p53 modulating agent, and a secondary, cell-based assay, such as an apoptosis or hypoxic induction assay (described below), may be used to further characterize the candidate p53 modulating agent. Many different assays for kinases have been reported in the literature and are well known to those skilled in the art (e.g. U.S. Pat. No. 6,165,992; Zhu et al., Nature Genetics (2000) 26:283-289; and WO0073469). Radioassays, which monitor the transfer of a gamma phosphate are frequently used. For instance, a scintillation assay for p56 (lck) kinase activity monitors the transfer of the gamma phosphate from gamma-33P ATP to a biotinylated peptide substrate; the substrate is captured on a streptavidin coated bead that transmits the signal (Beveridge M et al., J Biomol Screen (2000) 5:205-212). This assay uses the scintillation proximity assay (SPA), in which only radio-ligand bound to receptors tethered to the surface of an SPA bead are detected by the scintillant immobilized within it, allowing binding to be measured without separation of bound from free ligand.

Apoptosis assays. Assays for apoptosis may be performed by terminal deoxynucleotidyl transferase-mediated digoxigenin-11-dUTP nick end labeling (TUNEL) assay. The TUNEL assay is used to measure nuclear DNA fragmentation characteristic of apoptosis (Lazebnik et al., 1994, Nature 371, 346), by following the incorporation of fluorescein-dUTP (Yonehara et al., 1989, J. Exp. Med. 169, 1747). Apoptosis may further be assayed by acridine orange staining of tissue culture cells (Lucas, R., et al., 1998, Blood 15:4730-41). An apoptosis assay system may comprise a cell that expresses a MAP3K, and that optionally has defective p53 function (e.g. p53 is over-expressed or under-expressed relative to wild-type cells). A test agent can be added to the apoptosis assay system and changes in induction of apoptosis relative to controls where no test agent is added, identify candidate p53 modulating agents. In some embodiments of the invention, an apoptosis assay may be used as a secondary assay to test a candidate p53 modulating agents that is initially identified using a cell-free assay system. An apoptosis assay may also be used to test whether MAP3K function plays a direct role in apoptosis. For example, an apoptosis assay may be performed on cells that over- or under-express MAP3K relative to wild type cells. Differences in apoptotic response compared to wild type cells suggests that the MAP3K plays a direct role in the apoptotic response. Apoptosis assays are described further in U.S. Pat. No. 6,133,437.

Cell proliferation and cell cycle assays. Cell proliferation may be assayed via bromodeoxyuridine (BRDU) incorporation. This assay identifies a cell population undergoing DNA synthesis by incorporation of BRDU into newly-synthesized DNA. Newly-synthesized DNA may then be detected using an anti-BRDU antibody (Hoshino et al., 1986, Int. J. Cancer 38, 369; Campana et al., 1988, J. Immunol. Meth. 107, 79), or by other means.

Cell Proliferation may also be examined using [$^3$H]-thymidine incorporation (Chen, J., 1996, Oncogene 13:1395-403; Jeoung, J., 1995, J. Biol. Chem. 270:18367-73). This assay allows for quantitative characterization of S-phase DNA syntheses. In this assay, cells synthesizing DNA will incorporate [$^3$H]-thymidine into newly synthesized DNA. Incorporation can then be measured by standard techniques such as by counting of radioisotope in a scintillation counter (e.g., Beckman LS 3800 Liquid Scintillation Counter).

Cell proliferation may also be assayed by colony formation in soft agar (Sambrook et al., Molecular Cloning, Cold Spring Harbor (1989)). For example, cells transformed with MAP3K are seeded in soft agar plates, and colonies are measured and counted after two weeks incubation.

Involvement of a gene in the cell cycle may be assayed by flow cytometry (Gray J W et al. (1986) Int J Radiat Biol Relat Stud Phys Chem Med 49:237-55). Cells transfected with a MAP3K may be stained with propidium iodide and evaluated in a flow cytometer (available from Becton Dickinson).

Accordingly, a cell proliferation or cell cycle assay system may comprise a cell that expresses a MAP3K, and that optionally has defective p53 function (e.g. p53 is over-expressed or under-expressed relative to wild-type cells). A test agent can be added to the assay system and changes in cell proliferation or cell cycle relative to controls where no test agent is added, identify candidate p53 modulating agents. In some embodiments of the invention, the cell proliferation or cell cycle assay may be used as a secondary assay to test a candidate p53 modulating agents that is initially identified using another assay system such as a cell-free kinase assay system. A cell proliferation assay may also be used to test whether MAP3K function plays a direct role in cell proliferation or cell cycle. For example, a cell proliferation or cell cycle assay may be performed on cells that over- or under-express MAP3K relative to wild type cells. Differences in proliferation or cell cycle compared to wild type cells suggests that the MAP3K plays a direct role in cell proliferation or cell cycle.

Angiogenesis. Angiogenesis may be assayed using various human endothelial cell systems, such as umbilical vein, coronary artery, or dermal cells. Suitable assays include Alamar Blue based assays (available from Biosource International) to measure proliferation; migration assays using fluorescent molecules, such as the use of Becton Dickinson Falcon HTS FluoroBlock cell culture inserts to measure migration of cells through membranes in presence or absence of angiogenesis enhancer or suppressors; and tubule formation assays based on the formation of tubular structures by endothelial cells on MATRIGEL® (Becton Dickinson). Accordingly, an angiogenesis assay system may comprise a cell that expresses a MAP3K, and that optionally has defective p53 function (e.g. p53 is over-expressed or under-expressed relative to wild-type cells). A test agent can be added to the angiogenesis assay system and changes in angiogenesis relative to controls where no test agent is added, identify candidate p53 modulating agents. In some embodiments of the invention, the angiogenesis assay may be used as a secondary assay to test a candidate p53 modulating agent that is initially identified using another assay system. An angiogenesis assay may also be used to test whether MAP3K function plays a direct role in cell proliferation. For example, an angiogenesis assay may be performed on cells that over- or under-express MAP3K relative to wild type cells. Differences in angiogenesis compared to wild type cells suggest that the MAP3K plays a direct role in angiogenesis.

Hypoxic induction. The alpha subunit of the transcription factor, hypoxia inducible factor-1 (HIF-1), is upregulated in tumor cells following exposure to hypoxia in vitro. Under hypoxic conditions, HIF-1 stimulates the expression of genes known to be important in tumour cell survival, such as those encoding glycolytic enzymes and VEGF. Induction of such genes by hypoxic conditions may be assayed by growing cells transfected with MAP3K in hypoxic conditions (such as with 0.1% O2, 5% CO2, and balance N2, generated in a NAPCO® 7001 incubator (Precision Scientific)) and normoxic conditions, followed by assessment of gene activity or expression by TAQMAN®. For example, a hypoxic induction assay system may comprise a cell that expresses a MAP3K, and that optionally has a mutated p53 (e.g. p53 is over-expressed or under-expressed relative to wild-type cells). A test agent can be added to the hypoxic induction assay system and changes in hypoxic response relative to controls where no test agent is added, identify candidate p53 modulating agents. In some embodiments of the invention, the hypoxic induction assay may be used as a secondary assay to test a candidate p53 modulating agent that is initially identified using another assay system. A hypoxic induction assay may also be used to test whether MAP3K function plays a direct role in the hypoxic response. For example, a hypoxic induction assay may be performed on cells that over- or under-express MAP3K relative to wild type cells. Differences in hypoxic response compared to wild type cells suggest that the MAP3K plays a direct role in hypoxic induction.

Cell adhesion. Cell adhesion assays measure adhesion of cells to purified adhesion proteins, or adhesion of cells to each other, in presence or absence of candidate modulating agents. Cell-protein adhesion assays measure the ability of agents to modulate the adhesion of cells to purified proteins. For example, recombinant proteins are produced, diluted to 2.5 g/mL in PBS, and used to coat the wells of a microtiter plate. The wells used for negative control are not coated. Coated wells are then washed, blocked with 1% BSA, and washed again. Compounds are diluted to 2× final test concentration and added to the blocked, coated wells. Cells are then added to the wells, and the unbound cells are washed off. Retained cells are labeled directly on the plate by adding a membrane-permeable fluorescent dye, such as calcein-AM, and the signal is quantified in a fluorescent microplate reader.

Cell-cell adhesion assays measure the ability of agents to modulate binding of cell adhesion proteins with their native ligands. These assays use cells that naturally or recombinantly express the adhesion protein of choice. In an exemplary assay, cells expressing the cell adhesion protein are plated in wells of a multiwell plate. Cells expressing the ligand are labeled with a membrane-permeable fluorescent dye, such as BCECF, and allowed to adhere to the monolayers in the presence of candidate agents. Unbound cells are washed off, and bound cells are detected using a fluorescence plate reader.

High-throughput cell adhesion assays have also been described. In one such assay, small molecule ligands and peptides are bound to the surface of microscope slides using a microarray spotter, intact cells are then contacted with the slides, and unbound cells are washed off. In this assay, not only the binding specificity of the peptides and modulators against cell lines are determined, but also the functional cell signaling of attached cells using immunofluorescence techniques in situ on the microchip is measured (Falsey J R et al., Bioconjug Chem. 2001 May-June; 12(3):346-53).

Primary Assays for Antibody Modulators

For antibody modulators, an appropriate primary assay test is a binding assay that tests the antibody's affinity to and specificity for the MAP3K protein. Methods for testing antibody affinity and specificity are well known in the art (Harlow and Lane, 1988, 1999, supra). The enzyme-linked immunosorbant assay (ELISA®) is a preferred method for detecting MAP3K-specific antibodies; others include FACS assays, radioimmunoassays, and fluorescent assays.

Primary Assays for Nucleic Acid Modulators

For nucleic acid modulators, primary assays may test the ability of the nucleic acid modulator to inhibit or enhance MAP3K gene expression, preferably mRNA expression. In general, expression analysis comprises comparing MAP3K expression in like populations of cells (e.g., two pools of cells that endogenously or recombinantly express MAP3K) in the presence and absence of the nucleic acid modulator. Methods for analyzing mRNA and protein expression are well known in the art. For instance, Northern blotting, slot blotting, ribonuclease protection, quantitative RT-PCR (e.g., using the TAQMAN®, PE APPLIED BIOSYSTEMS®), or microarray analysis may be used to confirm that MAP3K mRNA expression is reduced in cells treated with the nucleic acid modulator (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm D H and Guiseppi-Elie, A Curr Opin Biotechnol 2001, 12:41-47). Protein expression may also be monitored. Proteins are most commonly detected with specific antibodies or antisera directed against either the MAP3K protein or specific peptides. A variety of means including Western blotting, ELISA®, or in situ detection, are available (Harlow E and Lane D, 1988 and 1999, supra).

Secondary Assays

Secondary assays may be used to further assess the activity of MAP3K-modulating agent identified by any of the above methods to confirm that the modulating agent affects MAP3K in a manner relevant to the p53 pathway. As used herein, MAP3K-modulating agents encompass candidate clinical compounds or other agents derived from previously identified modulating agent. Secondary assays can also be used to test the activity of a modulating agent on a particular genetic or biochemical pathway or to test the specificity of the modulating agent's interaction with MAP3K.

Secondary assays generally compare like populations of cells or animals (e.g., two pools of cells or animals that endogenously or recombinantly express MAP3K) in the presence and absence of the candidate modulator. In general, such assays test whether treatment of cells or animals with a candidate MAP3K-modulating agent results in changes in the p53 pathway in comparison to untreated (or mock- or placebo-treated) cells or animals. Certain assays use "sensitized genetic backgrounds", which, as used herein, describe cells or animals engineered for altered expression of genes in the p53 or interacting pathways.

Cell-Based Assays

Cell based assays may use a variety of mammalian cell lines known to have defective p53 function (e.g. SAOS-2 osteoblasts, H1299 lung cancer cells, C33A and HT3 cervical cancer cells, HT-29 and DLD-1 colon cancer cells, among others, available from American Type Culture Collection (ATCC), Manassas, Va.). Cell based assays may detect endogenous p53 pathway activity or may rely on recombinant expression of p53 pathway components. Any of the aforementioned assays may be used in this cell-based format. Candidate modulators are typically added to the cell media but may also be injected into cells or delivered by any other efficacious means.

Animal Assays

A variety of non-human animal models of normal or defective p53 pathway may be used to test candidate MAP3K modulators. Models for defective p53 pathway typically use genetically modified animals that have been engineered to mis-express (e.g., over-express or lack expression in) genes involved in the p53 pathway. Assays generally require systemic delivery of the candidate modulators, such as by oral administration, injection, etc.

In a preferred embodiment, p53 pathway activity is assessed by monitoring neovascularization and angiogenesis. Animal models with defective and normal p53 are used to test the candidate modulator's effect on MAP3K in MATRIGEL® assays. MATRIGEL® is an extract of basement membrane proteins, and is composed primarily of laminin, collagen IV, and heparin sulfate proteoglycan. It is provided as a sterile liquid at 4° C., but rapidly forms a solid gel at 37° C. Liquid MATRIGEL® is mixed with various angiogenic agents, such as bFGF and VEGF, or with human tumor cells which over-express the MAP3K. The mixture is then injected subcutaneously (SC) into female athymic nude mice (Taconic, Germantown, N.Y.) to support an intense vascular response. Mice with MATRIGEL® pellets may be dosed via oral (PO), intraperitoneal (IP), or intravenous (IV) routes with the candidate modulator. Mice are euthanized 5-12 days post-injection, and the MATRIGEL® pellet is harvested for hemoglobin analysis (Sigma plasma hemoglobin kit). Hemoglobin content of the gel is found to correlate the degree of neovascularization in the gel.

In another preferred embodiment, the effect of the candidate modulator on MAP3K is assessed via tumorigenicity assays. In one example, xenograft human tumors are implanted SC into female athymic mice, 6-7 week old, as single cell suspensions either from a pre-existing tumor or from in vitro culture. The tumors which express the MAP3K endogenously are injected in the flank, $1 \times 10^5$ to $1 \times 10^7$ cells per mouse in a volume of 100 μL using a 27 gauge needle. Mice are then ear tagged and tumors are measured twice weekly. Candidate modulator treatment is initiated on the day the mean tumor weight reaches 100 mg. Candidate modulator is delivered IV, SC, IP, or PO by bolus administration. Depending upon the pharmacokinetics of each unique candidate modulator, dosing can be performed multiple times per day. The tumor weight is assessed by measuring perpendicular diameters with a caliper and calculated by multiplying the measurements of diameters in two dimensions. At the end of the experiment, the excised tumors maybe utilized for biomarker identification or further analyses. For immunohistochemistry staining, xenograft tumors are fixed in 4% paraformaldehyde, 0.1M phosphate, pH 7.2, for 6 hours at 4° C., immersed in 30% sucrose in PBS, and rapidly frozen in isopentane cooled with liquid nitrogen.

Diagnostic and Therapeutic Uses

Specific MAP3K-modulating agents are useful in a variety of diagnostic and therapeutic applications where disease or disease prognosis is related to defects in the p53 pathway, such as angiogenic, apoptotic, or cell proliferation disorders. Accordingly, the invention also provides methods for modulating the p53 pathway in a cell, preferably a cell pre-determined to have defective p53 function, comprising the step of administering an agent to the cell that specifically modulates MAP3K activity. Preferably, the modulating agent produces a detectable phenotypic change in the cell indicating that the p53 function is restored, i.e., for example, the cell undergoes normal proliferation or progression through the cell cycle.

The discovery that MAP3K is implicated in p53 pathway provides for a variety of methods that can be employed for the diagnostic and prognostic evaluation of diseases and disorders involving defects in the p53 pathway and for the identification of subjects having a predisposition to such diseases and disorders.

Various expression analysis methods can be used to diagnose whether MAP3K expression occurs in a particular sample, including Northern blotting, slot blotting, ribonuclease protection, quantitative RT-PCR, and microarray analysis. (e.g., Current Protocols in Molecular Biology (1994) Ausubel F M et al., eds., John Wiley & Sons, Inc., chapter 4; Freeman W M et al., Biotechniques (1999) 26:112-125; Kallioniemi O P, Ann Med 2001, 33:142-147; Blohm and Guiseppi-Elie, Curr Opin Biotechnol 2001, 12:41-47). Tissues having a disease or disorder implicating defective p53 signaling that express a MAP3K, are identified as amenable to treatment with a MAP3K modulating agent. In a preferred application, the p53 defective tissue overexpresses a MAP3K relative to normal tissue. For example, a Northern blot analysis of mRNA from tumor and normal cell lines, or from tumor and matching normal tissue samples from the same patient, using full or partial MAP3K cDNA sequences as probes, can determine whether particular tumors express or overexpress MAP3K. Alternatively, the TAQMAN® is used for quantitative RT-PCR analysis of MAP3K expression in cell lines, normal tissues and tumor samples (PE APPLIED BIOSYSTEMS®).

Various other diagnostic methods may be performed, for example, utilizing reagents such as the MAP3K oligonucleotides, and antibodies directed against a MAP3K, as described above for: (1) the detection of the presence of MAP3K gene mutations, or the detection of either over- or under-expression of MAP3K mRNA relative to the non-disorder state; (2) the detection of either an over- or an under-abundance of MAP3K gene product relative to the non-disorder state; and (3) the detection of perturbations or abnormalities in the signal transduction pathway mediated by MAP3K.

Thus, in a specific embodiment, the invention is drawn to a method for diagnosing a disease in a patient, the method comprising: a) obtaining a biological sample from the patient; b) contacting the sample with a probe for MAP3K expression; c) comparing results from step (b) with a control; and d) determining whether step (c) indicates a likelihood of disease. Preferably, the disease is cancer, most preferably a cancer as shown in TABLE 1. The probe may be either DNA or protein, including an antibody.

Examples

The following experimental section and examples are offered by way of illustration and not by way of limitation.

1. *Drosophila* p53 Screen

The *Drosophila* p53 gene was overexpressed specifically in the wing using the vestigial margin quadrant enhancer. Increasing quantities of *Drosophila* p53 (titrated using different strength transgenic inserts in 1 or 2 copies) caused deterioration of normal wing morphology from mild to strong, with phenotypes including disruption of pattern and polarity of wing hairs, shortening and thickening of wing veins, progressive crumpling of the wing and appearance of dark "death" inclusions in wing blade. In a screen designed to identify enhancers and suppressors of *Drosophila* p53, homozygous females carrying two copies of p53 were crossed to 5663 males carrying random insertions of a piggyBac transposon (Fraser M et al., Virology (1985) 145:356-361). Progeny containing insertions were compared to non-insertion-bearing sibling progeny for enhancement or suppression of the p53 phenotypes. Sequence information surrounding the piggyBac insertion site was used to identify the modifier genes. Modifiers of the wing phenotype were identified as members of the p53 pathway. CG8789 was an enhancer of the wing phenotype. Human orthologs of the modifiers, are referred to herein as MAP3K.

BLAST analysis (Altschul et al., supra) was employed to identify Targets from *Drosophila* modifiers. [For example, representative sequences from MAP3K, GI #5454184 (SEQ ID NO:8) and GI #4758696 (SEQ ID NO:9) share 52% and 37% amino acid identity, respectively, with the *Drosophila*.CG8789.

Various domains, signals, and functional subunits in proteins were analyzed using the PSORT (Nakai K., and Horton P., Trends Biochem Sci, 1999, 24:34-6; Kenta Nakai, Protein sorting signals and prediction of subcellular localization, Adv. Protein Chem. 54, 277-344 (2000)), PFAM (Bateman A., et al., Nucleic Acids Res, 1999, 27:260-2; SMART (Ponting C P, et al., SMART: identification and annotation of domains from signaling and extracellular protein sequences. Nucleic Acids Res. 1999 Jan. 1; 27(1):229-32), TM-HMM (Erik L. L. Sonnhammer, Gunnar von Heijne, and Anders Krogh: A hidden Markov model for predicting transmembrane helices in protein sequences. In Proc. of Sixth Int. Conf. on Intelligent Systems for Molecular Biology, p 175-182 Ed J. Glasgow, T. Littlejohn, F. Major, R. Lathrop, D. Sankoff, and C. Sensen Menlo Park, Calif.: AAAI Press, 1998), and dust (Remm M, and Sonnhammer E. Classification of transmembrane protein families in the *Caenorhabditis elegans* genome and identification of human orthologs. Genome Res. 2000 November; 10(11):1679-89) programs. Using PFAM, the kinase domain of MAP3K from GI # 5454184 (SEQ ID NO:8) is located at approximately amino acid residues 125-366 (PFAM 00069). Likewise, the kinase domain of MAP3K from GI # 4758696 (SEQ ID NO:9) is located at approximately amino acid residues 168-409.

II. High-Throughput In Vitro Fluorescence Polarization Assay

Fluorescently-labeled MAP3K peptide/substrate are added to each well of a 96-well microtiter plate, along with a test agent in a test buffer (10 mM HEPES, 10 mM NaCl, 6 mM magnesium chloride, pH 7.6). Changes in fluorescence polarization, determined by using a Fluorolite FPM-2 Fluorescence Polarization Microtiter System (Dynatech Laboratories, Inc), relative to control values indicates the test compound is a candidate modifier of MAP3K activity.

III. High-Throughput In Vitro Binding Assay.

$^{33}$P-labeled MAP3K peptide is added in an assay buffer (100 mM KCl, 20 mM HEPES pH 7.6, 1 mM $MgCl_2$, 1% glycerol, 0.5% NP-40, 50 mM beta-mercaptoethanol, 1 mg/ml BSA, cocktail of protease inhibitors) along with a test agent to the wells of a Neutralite-avidin coated assay plate and incubated at 25° C. for 1 hour. Biotinylated substrate is then added to each well and incubated for 1 hour. Reactions are stopped by washing with PBS, and counted in a scintillation counter. Test agents that cause a difference in activity relative to control without test agent are identified as candidate p53 modulating agents.

IV. Immunoprecipitations and Immunoblotting

For coprecipitation of transfected proteins, 3×10⁶ appropriate recombinant cells containing the MAP3K proteins are plated on 10-cm dishes and transfected on the following day with expression constructs. The total amount of DNA is kept constant in each transfection by adding empty vector. After 24 h, cells are collected, washed once with phosphate-buffered saline and lysed for 20 min on ice in 1 ml of lysis buffer containing 50 mM Hepes, pH 7.9, 250 mM NaCl, 20 mM-glycerophosphate, 1 mM sodium orthovanadate, 5 mM p-nitrophenyl phosphate, 2 mM dithiothreitol, protease inhibitors (complete, Roche Molecular Biochemicals), and 1% Nonidet P-40. Cellular debris is removed by centrifugation twice at 15,000×g for 15 min. The cell lysate is incubated with 25 µl of M2 beads (Sigma) for 2 h at 4° C. with gentle rocking.

After extensive washing with lysis buffer, proteins bound to the beads are solubilized by boiling in SDS sample buffer, fractionated by SDS-polyacrylamide gel electrophoresis, transferred to polyvinylidene difluoride membrane and blotted with the indicated antibodies. The reactive bands are visualized with horseradish peroxidase coupled to the appropriate secondary antibodies and the enhanced chemiluminescence (ECL) Western blotting detection system (Amersham Pharmacia Biotech).

V. Kinase Assay

A purified or partially purified MAP3K is diluted in a suitable reaction buffer, e.g., 50 mM Hepes, pH 7.5, containing magnesium chloride or manganese chloride (1-20 mM) and a peptide or polypeptide substrate, such as myelin basic protein or casein (1-10 µg/ml). The final concentration of the kinase is 1-20 nM. The enzyme reaction is conducted in microtiter plates to facilitate optimization of reaction conditions by increasing assay throughput. A 96-well microtiter plate is employed using a final volume 30-100 µl. The reaction is initiated by the addition of $^{33}$P-gamma-ATP (0.5 µCi/ml) and incubated for 0.5 to 3 hours at room temperature. Negative controls are provided by the addition of EDTA, which chelates the divalent cation ($Mg^{2+}$ or $Mn^{2+}$) required for enzymatic activity. Following the incubation, the enzyme reaction is quenched using EDTA. Samples of the reaction are transferred to a 96-well glass fiber filter plate (MultiScreen, Millipore). The filters are subsequently washed with phosphate-buffered saline, dilute phosphoric acid (0.5%) or other suitable medium to remove excess radiolabeled ATP. Scintillation cocktail is added to the filter plate and the incorporated radioactivity is quantitated by scintillation counting (Wallac/Perkin Elmer). Activity is defined by the amount of radioactivity detected following subtraction of the negative control reaction value (EDTA quench).

VI. Expression Analysis

All cell lines used in the following experiments are NCI (National Cancer Institute) lines, and are available from ATCC$^{SM}$ (American Type Culture Collection, Manassas, Va. 20110-2209). Normal and tumor tissues were obtained from Impath, UC Davis, CLONTECH™, STRATAGENE®, Ardais, Genome Collaborative, and AMBION™.

TAQMAN® analysis was used to assess expression levels of the disclosed genes in various samples.

RNA was extracted from each tissue sample using QIAGEN™ (Valencia, Calif.) RNEASY® kits, following manufacturer's protocols, to a final concentration of 50 ng 4 ul. Single stranded cDNA was then synthesized by reverse transcribing the RNA samples using random hexamers and 50 Ong of total RNA per reaction, following protocol 430-4965 of APPLIED BIOSYSTEMS™ (Foster City, Calif.).

Primers for expression analysis using TAQMAN™ assay (APPLIED BIOSYSTEMS™, Foster City, Calif.) were prepared according to the TAQMAN™ protocols, and the following criteria: a) primer pairs were designed to span introns to eliminate genomic contamination, and b) each primer pair produced only one product.

TAQMAN™ reactions were carried out following manufacturer's protocols, in 25 µl total volume for 96-well plates and 10 µl total volume for 384-well plates, using 300 nM primer and 250 nM probe, and approximately 25 ng of cDNA. The standard curve for result analysis was prepared using a universal pool of human cDNA samples, which is a mixture of cDNAs from a wide variety of tissues so that the chance that a target will be present in appreciable amounts is good. The raw data were normalized using 18S rRNA (universally expressed in all tissues and cells).

For each expression analysis, tumor tissue samples were compared with matched normal tissues from the same patient. A gene was considered overexpressed in a tumor when the level of expression of the gene was 2 fold or higher in the tumor compared with its matched normal sample. In cases where normal tissue was not available, a universal pool of cDNA samples was used instead. In these cases, a gene was considered overexpressed in a tumor sample when the difference of expression levels between a tumor sample and the average of all normal samples from the same tissue type was greater than 2 times the standard deviation of all normal samples (i.e., Tumor−average(all normal samples)>2× STDEV(all normal samples)).

Results are shown in Table 1. Results from various batches of mRNA are represented for each batch. Data presented in bold indicate that greater than 50% of tested tumor samples of the tissue type indicated in row 1 exhibited over expression of the gene listed in column 1, relative to normal samples. Underlined data indicates that between 25% to 49% of tested tumor samples exhibited over expression. A modulator identified by an assay described herein can be further validated for therapeutic effect by administration to a tumor in which the gene is overexpressed. A decrease in tumor growth confirms therapeutic utility of the modulator. Prior to treating a patient with the modulator, the likelihood that the patient will respond to treatment can be diagnosed by obtaining a tumor sample from the patient, and assaying for expression of the gene targeted by the modulator. The expression data for the gene(s) can also be used as a diagnostic marker for disease progression. The assay can be performed by expression analysis as described above, by antibody directed to the gene target, or by any other available detection method.

TABLE 1

|  |  | breast |  | colon |  | lung |  | ovary |
|---|---|---|---|---|---|---|---|---|
| GI#5454183 (SEQ ID NO: 1) | TaqExp__100501 | 2 | 11 | . 4 | 30 | . 1 | 13 | . 1 | 7 |
| GI#13645287 (SEQ ID NO: 4) | TaqExp__100501 | 3 | 11 | . 1 | 30 | . 2 | 13 | . 3 | 7 |

What is claimed is:

1. A method of identifying a candidate p53 pathway modulating agent, said method comprising the steps of:
    (a) providing an assay system comprising a mitogen activated protein kinase kinase kinase (MAP3K) nucleic acid, wherein the MAP3K nucleic acid comprises SEQ ID NO:1, SEQ ID NO:4, or SEQ ID NO:5;
    (b) contacting the assay system with a test agent;
    (c) measuring the expression of the MAP3K nucleic acid in the presence or absence of the test agent of step (b); and
    (d) identifying the test agent as a candidate p53 pathway modulating agent by determining a change in the expression of MAP3K nucleic acid in the presence of said test agent compared to the absence of said test agent.

2. The method of claim 1, wherein the assay system comprises cultured cells that express the MAP3K polypeptide.

3. The method of claim 2, wherein the cultured cells additionally have defective p53 function.

4. The method of claim 1 wherein the assay system includes a screening assay comprising a MAP3K polypeptide, and the candidate test agent is a small molecule modulator.

5. The method of claim 4 wherein the assay is a kinase assay.

6. The method of claim 1 wherein the assay system includes a binding assay comprising a MAP3K polypeptide and the candidate test agent is an antibody.

7. The method of claim 1, wherein the assay system includes an expression assay comprising any of SEQ ID NOs: 1, 4, or 5 and the candidate test agent is a nucleic acid modulator.

8. The method of claim 7, wherein the nucleic acid modulator is an antisense oligomer.

9. The method of claim 7, wherein the nucleic acid modulator is a phosphothioate morpholino (PMO).

10. The method of claim 1 additionally comprising: (d) administering the candidate p53 pathway modulating agent identified in (c) to a model system comprising cells defective in p53 function and detecting a phenotypic change in the model system that indicates that the p53 function is restored.

11. The method of claim 10 wherein the model system is a mouse model with defective p53 function.

12. The method of claim 1, comprising the additional steps of:
    (d) providing a second assay system comprising cultured cells expressing said MAP3K, wherein the second assay is capable of detecting a change in the p53 pathway;
    (e) contacting the second assay system with the test agent of (b); and
    (f) measuring the p53 pathway in the second assay system in the presence or absence of the test agent of (b), wherein a change in the p53 pathway in the presence of said test agent confirms the test agent as a candidate p53 modulating agent.

* * * * *

SEQUENCE LISTING

<160> NUMBER OF SEQ ID NOS: 9

<210> SEQ ID NO 1
<211> LENGTH: 3365
<212> TYPE: DNA
<213> ORGANISM: Homo sapiens

<400> SEQUENCE: 1

| | | | | | | |
|---|---|---|---|---|---|---|
| agcatccgga | gcggagctgc | agcagcgccg | ccttttgtgc | tgcggccgcg | gagccccga | 60 |
| gggcccagtg | ttcaccatca | taccaggggc | cagaggcgat | ggcttgcctc | catgagaccc | 120 |
| gaacaccctc | tccttccttt | gggggctttg | tgtctaccct | aagtgaggca | tccatgcgca | 180 |
| agctggaccc | agacacttct | gactgcactc | ccgagaagga | cctgacgcct | acccatgtcc | 240 |
| tgcagctaca | tgagcaggat | gcaggggggcc | caggggggagc | agctgggtca | cctgagagtc | 300 |
| gggcatccag | agttcgagct | gacgaggtgc | gactgcagtg | ccagagtggc | agtggcttcc | 360 |
| ttgagggcct | ctttggctgc | ctgcgccctg | tctggaccat | gattggcaaa | gcctactcca | 420 |
| ctgagcacaa | gcagcagcag | gaagaccttt | ggaggtccc | ctttgaggaa | atcctggacc | 480 |
| tgcagtgggt | gggctcaggg | gcccaggtg | ctgtcttcct | ggggcgcttc | cacggggagg | 540 |
| aggtggctgt | gaagaaggtg | cgagacctca | aagaaaccga | catcaagcac | ttgcgaaagc | 600 |
| tgaagcaccc | caacatcatc | actttcaagg | gtgtgtgcac | ccaggctccc | tgctactgca | 660 |
| tcctcatgga | gttctgcgcc | cagggccagc | tgtatgaggt | actgcgggct | ggccgccctg | 720 |
| tcaccccctc | cttactggtt | gactggtcca | tgggcatcgc | tggtggcatg | aactacctgc | 780 |
| acctgcacaa | gattatccac | agggatctca | agtcacccaa | catgctaatc | acctacgacg | 840 |
| atgtggtgaa | gatctcagat | tttggcactt | ccaaggagct | gagtgacaag | agcaccaaga | 900 |
| tgtcctttgc | agggacagta | gcctggatgg | cccctgaggt | gatccgcaat | gaacctgtgt | 960 |
| ctgagaaggt | cgacatctgg | tcctttggcg | tggtgctatg | ggaactgctg | actggtgaga | 1020 |
| tccccctacaa | agacgtagat | tcctcagcca | ttatctgggg | tgtgggaagc | aacagtctcc | 1080 |
| atctgccccgt | gccctccagt | tgcccagatg | gtttcaagat | cctgcttcgc | cagtgctgga | 1140 |
| atagcaaacc | acgaaatcgc | ccatcattcc | gacagatcct | gctgcatctg | gacattgcct | 1200 |
| cagctgatgt | actctccaca | ccccaggaga | cttactttaa | gtcccaggca | gagtggcggg | 1260 |
| aagaagtaaa | actgcacttt | gaaaagatta | agtcagaagg | gacctgtctg | caccgcctag | 1320 |
| aagaggaact | ggtgatgagg | aggagggagg | agctcagaca | cgccctggac | atcagggagc | 1380 |
| actatgaaag | gaagctggag | agagccaaca | acctgtatat | ggaacttaat | gccctcatgt | 1440 |
| tgcagctgga | actcaaggag | agggagctgc | tcaggcgaga | gcaagcttta | gagcggaggt | 1500 |
| gcccaggcct | gctgaagcca | ccccttccc | ggggcctcct | gcatggaaac | acaatggaga | 1560 |
| agcttatcaa | gaagaggaat | gtgccacaga | atctgtcacc | ccatagccaa | aggccagata | 1620 |
| tcctcaaggc | ggagtctttg | ctccctaaac | tagatgcagc | cctgagtggg | gtggggcttc | 1680 |
| ctgggtgtcc | taaggccccc | ccctcaccag | gacgagtcg | ccgtggcaag | cccgtcaccc | 1740 |
| gcaaggccag | cgccaagggg | agctgtgggg | acctgcctgg | gcttcgtaca | gctgtgccac | 1800 |
| cccatgaacc | tggaggacca | ggaagcccag | ggggcctagg | aggggaccc | tcagcctggg | 1860 |
| aggcctgccc | tcccgccctc | cgtgggcttc | atcatgacct | cctgctccgc | aaaatgtctt | 1920 |
| catcgtcccc | agacctgctg | tcagcagcac | tagggtcccg | ggggcggggg | gccacaggcg | 1980 |
| gagctgggga | tcctggctca | ccacctccgg | cccggggtga | caccccacca | agtgagggct | 2040 |

```
cagcccctgg ctccaccagc ccagattcac ctggggagc caaaggggaa ccacctcctc    2100
cagtagggcc tggtgaaggt gtggggcttc tgggaactgg aagggaaggg acctcaggcc    2160
ggggaggaag ccgggctggg tcccagcact tgaccccagc tgcactgctg tacagggctg    2220
ccgtcacccg aagtcagaaa cgtggcatct catcggaaga ggaggaagga gaggtagaca    2280
gtgaagtaga gctgacatca agccagaggt ggcctcagag cctgaacatg cgccagtcac    2340
tatctacctt cagctcagag aatccatcag atggggagga aggcacagct agtgaacctt    2400
cccccagtgg cacacctgaa gttggcagca ccaacactga tgagcggcca gatgagcggt    2460
ctgatgacat gtgctcccag ggctcagaaa tcccactgga cccacctcct tcagaggtca    2520
tccctggccc tgaacccagc tccctgccca ttccacacca ggaacttctc agagagcggg    2580
gccctcccaa ttctgaggac tcagactgtg acagcactga attggacaac tccaacagcg    2640
ttgatgcctt gcgccccccca gcttccctcc ctccatgaaa gccactcgta ttccttgtac    2700
atagagaaat atttatatgg attatatata tatacatata tatatatata tgcgccacat    2760
aatcaacaga aagatggggc tgtcccagcc gtaagtcagg ctcgagggag actgatcccc    2820
tgaccaattc acctgataaa ctctagggac actggcagct gtggaaatga atgaggcaca    2880
gccgtagagc tgtggctaag ggcaagcccc ttcctgcccc accccattcc ttatattcag    2940
caagcaacaa ggcaatagaa aagccagggt tgtctttata ttctttatcc ccaaataata    3000
gggggtgggg ggaggggcgg tgggagggc aggagagaaa accacttaga ctgcactttt    3060
ctgttccgtt tactctgttt acacattttg cacttgggag gagggaggct aaggctgggt    3120
cctcccctct gaggtttctc aggtggcaat gtaactcatt ttttgtccc accatttatc    3180 ttctctgccc aagccctgtc ttaaggccca ggggaggtt aggagactga tagcatgtga    3240
tggctcaggc tgaagaaccg gggttctgtt taagtccctg cttttatcct ggtgcctgat    3300
tggggtgggg actgtcctac tgtaaccct gtgaaaaacc ttgaaaaata acactccatg    3360
cagga                                                                3365
```

<210> SEQ ID NO 2
<211> LENGTH: 2830
<212> TYPE: DNA
<213> ORGANISM: Homo sapiens
<220> FEATURE:
<221> NAME/KEY: misc_feature
<222> LOCATION: (33)..(33)
<223> OTHER INFORMATION: "n" is A, C, G, or T

<400> SEQUENCE: 2

```
cgagggccca gtgttcacca tcataccagg ggncagaggc gatggcttgc ctccatgaga     60
cccgaacacc ctctccttcc tttgggggct ttgtgtctac cctaagtgag gcatccatgc    120
gcaagctgga cccagacact tctgactgca ctcccgagaa ggacctgacg cctacccagt    180
gtgtacttcg agatgtggta ccccttggtg ggcaggtgg ggagggccc agcccctccc    240 caggtggaga gccgccccct gagccttttg ccaacagtgt cctgcagcta catgagcagg    300
atgcaggggg cccagggga gcagctgggt caccctgagag tcgggcatcc agagttcgag    360
ctgacgaggt gcgactgcag tgccagagtg gcagtggctt ccttgagggc ctctttggct    420
gcctgcgccc tgtctggacc atgattgca aagcctactc cactgagcac aagcagcagc    480
aggaagacct ttgggaggtc cccttgagg aaatcctgga cctgcagtgg gtgggctcag    540
gggcccaggg tgctgtcttc ctggggcgct tccacggga ggaggtggct gtgaagaagg    600
tgcgagacct caaagaaacc gacatcaagc acttgcgaaa gctgaagcac cccaacatca    660
```

```
tcactttcaa gggtgtgtgc acccaggctc cctgctactg catcctcatg gagttctgcg     720
cccagggcca gctgtatgag gtactgcggg ctggccgccc tgtcacccc tccttactgg      780
ttgactggtc catgggcatc gctggtggca tgaactacct gcacctgcac aagattatcc     840
acagggatct caagtcaccc aacatgctaa tcacctacga cgatgtggtg aagatctcag     900
attttggcac ttccaaggag ctgagtgaca agagcaccaa gatgtccttt gcagggacag     960
tagcctggat ggcccctgag gtgatccgca atgaacctgt gtctgagaag gtcgacatct    1020
ggtcctttgg cgtggtgcta tgggaactgc tgactggtga gatccctac aaagacgtag     1080
attcctcagc cattatctgg ggtgtgggaa gcaacagtct ccatctgccc gtgccctcca    1140
gttgcccaga tggtttcaag atcctgcttc gccagtgctg gaatagcaaa ccacgaaatc    1200
gcccatcatt ccgacagatc ctgctgcatc tggacattgc ctcagctgat gtactctcca    1260
caccccagga gacttacttt aagtcccagg cagagtggcg ggaagaagta aaactgcact    1320
ttgaaaagat taagtcagaa gggacctgtc tgcaccgcct agaagaggaa ctggtgatga    1380
ggaggaggga ggagctcaga cacgccctgg acatcaggga gcactatgaa aggaagctgg    1440
agagagccaa caacctgtat atggaactta atgccctcat gttgcagctg gaactcaagg    1500
agagggagct gctcaggcga gagcaagctt tagagcggag gtgcccaggc ctgctgaagc    1560
cacacccttc ccggggcctc ctgcatggaa acacaatgga gaagcttatc aagaaggaga    1620
atgtgccaca gaagctgtca ccccatagca aaaggccaga tatcctcaag acggagtctt    1680
tgctccctaa actagatgca gccctgagtg gggtggggct tcctgggtgt cctaagggcc    1740
cccctcacc aggacggagt cgccgtggca agacccgtca ccgcaaggcc agcgccaagg     1800
ggagctgtgg ggacctgcct gggcttcgta cagctgtgcc accccatgaa cctggaggac    1860
caggaagccc aggggcccta ggaggggac cctcagcctg ggaggcctgc cctcccgccc     1920
tccgtgggct tcatcatgac ctcctgctcc gcaaaatgtc ttcatcgtcc ccagacctgc    1980
tgtcagcagc actagggtcc cggggccggg gggccacagg cggagctggg gatcctggct    2040
caccacctcc ggcccggggt gacacccac caagtgaggg ctcagcccct ggctccacca     2100
gcccagattc acctggggga gccaaagggg aaccacctcc tccagtaggg cctggtgaag    2160
gtgtgggct tctgggaact ggaagggaag ggacctcagg ccgggggagga agccgggctg    2220
ggtcccagca cttgaccca gctgcactgc tgtacagggc tgccgtcacc cgaagtcaga     2280
aacgtggcat ctcatcggaa gaggaggaag gagaggtaga cagtgaagta gagctgacat    2340
caagccagag gtggcctcag agcctgaaca tgcgccagtc actatctacc ttcagctcag    2400
agaatccatc agatggggag gaaggcacag ctagtgaacc ttcccccagt ggcacacctg    2460
aagttggcag caccaacact gatgagcggc cagatgagcg gtctgatgac atgtgctccc    2520
agggctcaga aatcccactg gacccacctc cttcagaggt catccctggc cctgaaccca    2580
gctccctgcc cattccacac caggaacttc tcagagagcg ggcccctccc aattctgagg    2640
actcagactg tgacagcact gaattggaca actccaacag cgttgatgcc ttgcggcccc    2700
cagcttccct ccctccatga aagccactcg tattccttgt acatagagaa atatttatat    2760
aaattatata tatatacata tatatatata tatgcgccac ataatcaaca gaaagatggg    2820
gctgtcccag                                                           2830
```

<210> SEQ ID NO 3
<211> LENGTH: 2732
<212> TYPE: DNA
<213> ORGANISM: Homo sapiens

```
<400> SEQUENCE: 3
cgagggccca gtgttcacca tcataccagg ggccagaggc gatggcttgc ctccatgaga    60
cccgaacacc ctctccttcc tttgggggct ttgtgtctac cctaagtgag gcatccatgc   120
gcaagctgga cccagacact tctgactgca ctcccgagaa ggacctgacg cctacccatg   180
tcctgcagct acatgagcag gatgcagggg gcccagggga agcagctggg tcacctgaga   240
gtcgggcatc cagagttcga gctgacgagg tgcgactgca gtgccagagt ggcagtggct   300
tccttgaggg cctctttggc tgcctgcgcc ctgtctggac catgattggc aaagcctact   360
ccactgagca caagcagcag caggaagacc tttgggaggt cccctttgag gaaatcctgg   420
acctgcagtg ggtgggctca ggggcccagg gtgctgtctt cctgggcgc ttccacgggg    480 aggaggtggc tgtgaagaag gtgcgagacc tcaaagaaac cgacatcaag cacttgcgaa   540
agctgaagca ccccaacatc atcactttca agggtgtgtg cacccaggct ccctgctact   600
gcatcctcat ggagttctgc gcccaggcc agctgtatga ggtactgcgg gctggccgcc    660
ctgtcacccc ctccttactg gttgactggt ccatgggcat cgctggtggc atgaactacc   720
tgcacctgca caagattatc cacagggatc tcaagtcacc caacatgcta atcacctacg   780
acgatgtggt gaagatctca gattttggca cttccaagga gctgagtgac aagagcacca   840
agatgtcctt tgcagggaca gtagcctgga tggcccctga ggtgatccgc aatgaacctg   900
tgtctgagaa ggtcgacatc tggtcctttg gcgtggtgct atgggaactg ctgactggtg   960 agatcccta caaagacgta gattcctcag ccattatctg gggtgtggga agcaacagtc   1020
tccatctgcc cgtgccctcc agttgcccag atggtttcaa gatcctgctt cgccagtgct   1080
ggaatagcaa accacgaaat cgcccatcat tccgacagat cctgctgcat ctggacattg   1140
cctcagctga tgtactctcc acaccccagg agacttactt taagtcccag gcagagtggc   1200
gggaagaagt aaaactgcac tttgaaaaga ttaagtcaga agggacctgt ctgcaccgcc   1260
tagaagagga actggtgatg aggaggaggg aggagctcag acacgccctg acatcaggg   1320 agcactatga aggaagctg gagagagcca caacctgta tatgaactt aatgccctca    1380 tgttgcagct ggaactcaag gagagggagc tgctcaggcg agagcaagct ttagagcgga   1440
ggtgcccagg cctgctgaag ccacaccctt cccggggcct cctgcatgga aacacaatgg   1500
agaagcttat caagaagagg aatgtgccac agaagctgtc accccatagc aaaaggccag   1560
atatcctcaa gacggagtct ttgctcccta aactagatgc agccctgagt ggggtggggc   1620
ttcctgggtg tcctaaggc cccccctcac caggacggag tcgccgtggc aagaccgtc    1680 accgcaaggc cagcgccaag gggagctgtg gggacctgcc tgggcttcgt acagctgtgc   1740 cacccatga acctggagga ccaggaagcc caggggcct aggagggga ccctcagcct    1800 gggaggcctg ccctcccgcc ctccgtgggc ttcatcatga cctcctgctc cgcaaaatgt   1860
cttcatcgtc cccagacctg ctgtcagcag cactagggtc ccggggccgg ggggccacag   1920
gcggagctgg ggatcctggc tcaccacctc cggcccgggg tgacacccca ccaagtgagg   1980
gctcagcccc tggctccacc agcccagatt cacctggggg agccaaaggg gaaccacctc   2040
ctccagtagg gcctggtgaa ggtgtgggc ttctgggaac tggaagggaa gggacctcag    2100
gccggggagg aagccgggct gggtcccagc acttgacccc agctgcactg ctgtacaggg   2160
ctgccgtcac ccgaagtcag aaacgtggca tctcatcgga agaggaggaa ggagaggtag   2220
acagtgaagt agagctgaca tcaagccaga ggtggcctca gagcctgaac atgccccagt   2280
cactatctac cttcagctca gagaatccat cagatgggga ggaaggcaca gctagtgaac   2340
```

| | |
|---|---|
| cttcccccag tggcacacct gaagttggca gcaccaacac tgatgagcgg ccagatgagc | 2400 |
| ggtctgatga catgtgctcc cagggctcag aaatcccact ggacccacct ccttcagagg | 2460 |
| tcatccctgg ccctgaaccc agctccctgc ccattccaca ccaggaactt ctcagagagc | 2520 |
| ggggcccctcc caattctgag gactcagact gtgacagcac tgaattggac aactccaaca | 2580 |
| gcgttgatgc cttgcggccc ccagcttccc tccctccatg aaagccactc gtattccttg | 2640 |
| tacatagaga aatatttata taaattatat atatatacat atatatatat atatgcgcca | 2700 |
| cataatcaac agaaagatgg ggctgtccag cc | 2732 |

<210> SEQ ID NO 4
<211> LENGTH: 3378
<212> TYPE: DNA
<213> ORGANISM: Homo sapiens

<400> SEQUENCE: 4

| | |
|---|---|
| gttttggagc cctctcttaa gtcagaactc tgtcccaaaa atcttctgag tgtcatctca | 60 |
| ggactttggt tatactcatg gcacgatggc caactttcag gagcacctga gctgctcctc | 120 |
| ttctccacac ttacccttca gtgaaagcaa aaccttcaat ggactacaag atgagctcac | 180 |
| agctatgggg aaccacccttt ctcccaagct gctcgaggac cagcaggaaa aggggatggt | 240 |
| acgaacagag ctaatcgaga gcgtgcacag ccccgtcacc acaacagtgt tgacgagcgt | 300 |
| aagtgaggat tccagggacc agtttgagaa cagcgttctt cagctaaggg aacacgatga | 360 |
| atcagagacg gcggtgtctc aggggaacag caacacggtg gacggagaga gcacaagcgg | 420 |
| aactgaagac ataaagattc agttcagcag gtcaggcagt ggcagtggtg ggtttcttga | 480 |
| aggactattt ggatgcttaa ggcctgtatg gaatatcatt gggaaggcat attccactga | 540 |
| ttacaaattg cagcagcaag atacttggga agtgccattt gaggagatct cagagctgca | 600 |
| gtggctgggt agtggagccc aaggagcggt cttcttgggc aagttccggg cggaagaggt | 660 |
| ggccatcaag aaagtgagag aacagaatga gacggatatc aagcatttga ggaagttgaa | 720 |
| gcaccctaac atcatcgcat tcaagggtgt ttgtactcag gccccatgtt attgtattat | 780 |
| catggaatac tgtgccccatg gacaactcta cgaggtctta cgagctggca ggaagatcac | 840 |
| acctcgattg ctagtagact ggtccacagg aattgcaagt ggaatgaatt atttgcacct | 900 |
| ccataaaatt attcatcgtg atctcaaatc acctaatgtt ttagtgaccc acacagatgc | 960 |
| ggtaaaaatt tcagattttg gtacatctaa ggaactcagt gacaaaagta ccaagatgtc | 1020 |
| atttgctggc acggtcgcat ggatggcgcc agaggtgata cggaatgaac ctgtctctga | 1080 |
| aaaagttgat atatggtctt ttggagtggt gctttgggag ctgctgacag gagagatccc | 1140 |
| ttacaaagat gtagattctt cagccattat ctggggtgtt ggaagcaaca gcctccacct | 1200 |
| tccagttcct tccacttgcc ctgatggatt caaaatcctt atgaaacaga cgtggcagag | 1260 |
| taaacctcga aaccgacctt cttttcggca gacactcatg catttagaca ttgcctctgc | 1320 |
| agatgtactt gccaccccac aagaaactta cttcaagtct caggctgaat ggagagaaga | 1380 |
| agtgaaaaaa cattttgaga agatcaaaag tgaaggaact tgtatacacc ggttagatga | 1440 |
| agaactgatt cgaaggcgca gagaagagct caggcatgcg ctggatattc gtgaacacta | 1500 |
| tgagcggaag cttgagcggg cgaataattt atacatggaa ttgagtgcca tcatgctgca | 1560 |
| gctagaaatg cgggagaagg agctcattaa gcgtgagcaa gcagtggaaa agaagtatcc | 1620 |
| tgggacctac aaacgacacc ctgttcgtcc tatcatccat cccaatgcca tggagaaact | 1680 |
| catgaaaagg aaaggagtgc ctcacaaatc tgggatgcag accaaacggc cagacttgtt | 1740 |

```
gagatcagaa gggatcccca ccacagaagt ggctcccact gcatcccctt tgtccggaag    1800
tcccaaaatg tccacttcta gcagcaagag ccgatatcga agcaaaccac gccaccgccg    1860
agggaatagc agaggcagcc atagtgactt tgccgcaatc ttgaaaaacc agccagccca    1920
ggaaaattca ccccatccca cttacctgca ccaagctcaa tcccaatacc cttctcttca    1980
tcaccataat tctctgcagc agcaatacca gcagccccct cctgccatgt cccagagtca    2040
ccatcccaga ctcaatatgc acggacagga catagcaacc tgcgccaaca acctgaggta    2100
tttcggccca gcagcagccc tgcggagccc actcagcaac catgctcaga gacagctgcc    2160
cggctcgagc cctgacctca tctccacagc catggctgca gactgctgga gaagttctga    2220
gcctgacaag ggccaagctg gtccctgggg ctgttgccag gctgacgctt atgacccctg    2280
ccttcagtgc aggccagaac agtatgggtc cttagacata ccctctgctg agccagtggg    2340
gaggagccct gacctttcca agtcaccagc acataatcct ctcttggaaa acgcccagag    2400
ttctgagaaa acgaagaaa atgaattcag cggctgtagg tctgagtcat ccctcggcac    2460
ctctcatctc ggcacccctc cagcgctacc tcgaaaaaca aggcctctgc agaagagtgg    2520
agatgactcc tcagaagagg aagaagggga agtagatagt gaagttgaat tccacgaag    2580 acagaggccc catcgctgta tcagcagctg ccagtcatat tcaacctta gctctgagaa    2640 tttctctgtg tctgatggag aagagggaaa taccagtgac cactcaaaca gtcctgatga    2700
gttagctgat aaacttgaag accgcttggc agagaagcta gacgacctgc tgtcccagac    2760
gccagagatt cccattgaca tatcctcaca ctcggatggg ctctctgaca aggagtgtgc    2820
cgtgcgccgt gtgaagactc agatgtctct gggcaagctg tgtgtggagg aacgtggcta    2880 tgagaaccc atgcagtttg aagaatcgga ctgtgactct tcagatgggg agtgttctga    2940
tgccacagtt aggaccaata acactacag ctctgctacc tggtaatgaa ggaatacaca    3000
tcctgaagat ctcgtgacta tactggcatt tcagatccac cccaccccca gactcatccc    3060
actctctccc agcattttgt ctgggaagag agactacccc atctttacca cccctagaa    3120 atgagctgca ataacaggaa catgagactt cgcaaatctc tggaaaataa tatccaaatg    3180
aaattaagtc tcactgaaca tttcaatcaa gaatggcagg gatctatttt attgaatatt    3240
ctagctactg taacattgat atttattttt gtttgacatt ttaacacttt gtactgcaaa    3300
gagtgaacta tatatgagat agagagacaa taatttcttg caaaaaaaaa aagagataaa    3360
agaaagaaca gaaaaaaa                                                 3378

<210> SEQ ID NO 5
<211> LENGTH: 3569
<212> TYPE: DNA
<213> ORGANISM: Homo sapiens
<220> FEATURE:
<221> NAME/KEY: misc_feature
<222> LOCATION: (3283)..(3283)
<223> OTHER INFORMATION: "n" is A, C, G, or T

<400> SEQUENCE: 5
aatttacatc cattcatgaa tctgtgacgt cagcaagcct ttgggctcct ttgcggtggg     60
ctggaggatt gtgtgggtgg aatccccctc ccctttattt ttccaattct gcaaggcttt    120
taaaattcac cttacatctt ttcaaagcaa gaaaatggaa cagcatgtgt aggaattctt    180
cgttgttgtt ttggagccct ctcttaagtc agaactctgt cccaaaaatc ttctgagtgt    240
catctcagga ctttggttat actcatggca cgatggccaa cttttcaggag cacctgagct    300 gctcctcttc tccacactta cccttcagtg aaagcaaaac cttcaatgga ctacaagatg    360
```

```
agctcacagc tatggggaac cacccttctc ccaagctgct cgaggaccag caggaaaagg    420
ggatggtacg aacagagcta atcgagagcg tgcacagccc cgtcaccaca acagtgttga    480
cgagcgtaag tgaggattcc agggaccagt ttgagaacag cgttcttcag ctaagggaac    540
acgatgaatc agagacggcg tgtctcaggg gaacagcaa cacggtggac ggagagagca    600
caagcggaac tgaagacata aagattcagt tcagcaggtc aggcagtggc agtggtgggt    660
ttcttgaagg actatttgga tgcttaaggc ctgtatggaa tatcattggg aaggcatatt    720
ccactgatta caaattgcag cagcaagata cttgggaagt gccatttgag gagatctcag    780
agctgcagtg gctgggtagt ggagcccaag gagcggtctt cttgggcaag ttccgggcgg    840
aagaggtggc catcaagaaa gtgagagaac agaatgagac ggatatcaag catttgagga    900
agttgaagca ccctaacatc atcgcattca agggtgtttg tactcaggcc ccatgttatt    960
gtattatcat ggaatactgt gcccatggac aactctacga ggtcttacga gctggcagga   1020
agatcacacc tcgattgcta gtagactggt ccacaggaat tgcaagtgga atgaattatt   1080
tgcacctcca taaaattatt catcgtgatc tcaaatcacc taatgtttta gtgacccaca   1140
cagatgcggt aaaaatttca gattttggta catctaagga actcagtgac aaaagtacca   1200
agatgtcatt tgctggcacg gtcgcatgga tggcgccaga ggtgatacgg aatgaacctg   1260
tctctgaaaa agttgatata tggtcttttg gagtggtgct ttgggagctg ctgacaggag   1320
agatccctta caaagatgta gattcttcag ccattatctg gggtgttgga agcaacagcc   1380
tccaccttcc agttccttcc acttgccctg atggattcaa aatccttatg aaacagacgt   1440
ggcagagtaa acctcgaaac cgaccttctt ttcggcagac actcatgcat ttagacattg   1500
cctctgcaga tgtacttgcc accccacaag aaacttactt caagtctcag gctgaatgga   1560
gagaagaagt gaaaaaacat tttgagaaga tcaaaagtga aggaacttgt atacaccggt   1620
tagatgaaga actgattcga aggcgcagag aagagctcag gcatgcgctg gatattcgtg   1680
aacactatga gcggaagctt gagcgggcga ataatttata catggaattg agtgccatca   1740
tgctgcagct agaaatgcgg gagaaggagc tcattaagcg tgagcaagca gtggaaaaga   1800
agtatcctgg gacctacaaa cgacaccctg ttcgtcctat catccatccc aatgccatgg   1860
agaaactcat gaaaggaaa ggagtgcctc acaaatctgg gatgcagacc aaacggccag   1920
acttgttgag atcagaaggg atccccacca cagaagtggc tcccactgca tccccttttgt   1980 ccggaagtcc caaaatgtcc acttctagca gcaagagccg atatcgaagc aaaccacgcc   2040
accgccgagg gaatagcaga ggcagccata gtgactttgc cgcaatcttg aaaaccagc    2100 cagcccagga aaattcaccc catcccactt acctgcacca agctcaatcc caataccctt   2160
ctcttcatca ccataattct ctgcagcagc aataccagca gcccctcct gcatgtccc     2220 agagtcacca tcccagactc aatatgcacg gacaggacat agcaacctgc gccaacaacc   2280
tgaggtattt cggcccagca gcagccctgc ggagcccact cagcaaccat gctcagagac   2340
agctgcccgg ctcgagccct gacctcatct ccacagccat ggctgcagac tgctggagaa   2400
gttctgagcc tgacaagggc caagctggtc cctgggctg ttgccaggct gacgcttatg    2460 accccctgcct tcagtgcagg ccagaacagt atgggtcctt agacataccc tctgctgagc   2520
cagtggggag gagcccctgac cttttccaagt caccagcaca taatcctctc ttggaaaacg   2580
cccagagttc tgagaaaacg gaagaaaatg aattcagcgg ctgtaggtct gagtcatccc   2640
tcggcacctc tcatctcggc accccctccag cgctacctcg aaaaacaagg cctctgcaga   2700
agagtggaga tgactcctca gaagaggaag aaggggaagt agatagtgaa gttgaatttc   2760
```

| | |
|---|---|
| cacgaagaca gaggccccat cgctgtatca gcagctgcca gtcatattca acctttagct | 2820 |
| ctgagaattt ctctgtgtct gatggagaag agggaaatac cagtgaccac tcaaacagtc | 2880 |
| ctgatgagtt agctgataaa cttgaagacc gcttggcaga aagctagac gacctgctgt | 2940 |
| cccagacgcc agagattccc attgacatat cctcacactc ggatgggctc tctgacaagg | 3000 |
| agtgtgccgt gcgccgtgtg aagactcaga tgtctctggg caagctgtgt gtggaggaac | 3060 |
| gtggctatga gaaccccatg cagtttgaag aatcggactg tgactcttca gatggggagt | 3120 |
| gttctgatgc cacagttagg accaataaac actacagctc tgctacctgg taatgaagga | 3180 |
| atacacatcc tgaagatctc gtgactatac tggcatttca gatccacccc accccagac | 3240 |
| tcatcccact ctctcccagc attttgtctg ggaagagaga ctnacccatc tttacccacc | 3300 |
| ccctagaaat gagctgcaat aacaggaaca tgagacttcg caaatctctg gaaaataata | 3360 |
| tccaaatgaa attaagtctc actgaacatt tcaatcaaga atggcaggga tctattttat | 3420 |
| tgaatattct agctactgta acattgatat ttattttgt ttgacatttt aacactttgt | 3480 |
| actgcaaaga gtgaactata tatgagatag agagacaata atttcttgca aaaaaaaaa | 3540 |
| gagataaaag aagaacaaa aaaaaaaaa | 3569 |

<210> SEQ ID NO 6
<211> LENGTH: 2910
<212> TYPE: DNA
<213> ORGANISM: Homo sapiens

<400> SEQUENCE: 6

| | |
|---|---|
| acgatggcca actttcagga gcacctgagc tgctcctctt ctccacactt acccttcagt | 60 |
| gaaagcaaaa ccttcaatgg actacaagat gagctcacag ctatggggaa ccacccttct | 120 |
| cccaagctgc tcgaggacca gcaggaaaag gggatggtac gaacagagct aatcgagagc | 180 |
| gtgcacagcc ccgtcaccac aacagtgttg acgagcgtaa gtgaggattc cagggaccag | 240 |
| tttgagaaca gcgttcttca gctaagggaa cacgatgaat cagagacggc ggtgtctcag | 300 |
| gggaacagca acacggtgga cggagagagc caagtggaa ctgaagacat aaagattcag | 360 |
| ttcagcaggt caggcagtgg cagtggtggg tttcttgaag gactatttgg atgcttaagg | 420 |
| cctgtatgga atatcattgg gaaggcatat tccactgatt acaaattgca gcagcaagat | 480 |
| acttgggaag tgccatttga ggagatctca gagctgcagt ggctgggtag tggagcccaa | 540 |
| ggagcggtct tcttgggcaa gttccggggcg aagaggtgg ccatcaagaa agtgagagaa | 600 |
| cagaatgaga cggatatcaa gcatttgagg aagttgaagc accctaacat catcgcattc | 660 |
| aagggtgttt gtactcaggc cccatgttat tgtattatca tggaatactg tgcccatgga | 720 |
| caactctacg aggtcttacg agctggcagg aagatcacac ctcgattgct agtagactgg | 780 |
| tccacaggaa ttgcaagtgg aatgaattat ttgcacctcc ataaattat tcatcgtgat | 840 |
| ctcaaatcac ctaatgtttt agtgacccac acagatgcgg taaaaatttc agattttggt | 900 |
| acatctaagg aactcagtga caaaagtacc aagatgtcat tgctggcac ggtcgcatgg | 960 |
| atggcgccag aggtgatacg gaatgaacct gtctctgaaa agttgatat atggtctttt | 1020 |
| ggagtggtgc tttgggagct gctgacagga gagatccctt acaaagatgt agattcttca | 1080 |
| gccattatct ggggtgttgg aagcaacagc ctccaccttc cagttccttc cacttgccct | 1140 |
| gatggattca aaatccttat gaaacagacg tggcagagta accctcgaaa ccgaccttct | 1200 |
| tttcggcaga cactcatgca tttagacatt gcctctgcag atgtacttgc cacccacaa | 1260 |
| gaaacttact tcaagtctca ggctgaatgg agagaagaag tgaaaaaaca ttttgagaag | 1320 |

```
atcaaaagtg aaggaacttg tatacaccgg ttagatgaag aactgattcg aaggcgcaga    1380
gaagagctca ggcatgcgct ggatattcgt gaacactatg agcggaagct tgagcgggcg    1440
aataatttat acatggaatt gagtgccatc atgctgcagc tagaaatgcg ggagaaggag    1500
ctcattaagc gtgagcaagc agtggaaaag aagtatcctg ggacctacaa acgacaccct    1560
gttcgtccta tcatccatcc caatgccatg agaaactca tgaaaaggaa aggagtgcct     1620
cacaaatctg ggatgcagac caaacggcca gacttgttga gatcagaagg gatccccacc    1680
acagaagtgg ctcccactgc atccccttg tccggaagtc ccaaaatgtc cacttctagc     1740
agcaagagcc gatatcgaag caaaccacgc caccgccgag ggaatagcag aggcagccat    1800
agtgactttg ccgcaatctt gaaaaaccag ccagcccagg aaaattcacc ccatcccact    1860
tacctgcacc aagctcaatc ccaatacccct tctcttcatc accataattc tctgcagcag   1920
caataccagc agccccctcc tgccatgtcc cagagtcacc atcccagact caatatgcac    1980
ggacaggaca tagcaacctg cgccaacaac ctgaggtatt tcggcccagc agcagccctg    2040
cggagcccac tcagcaacca tgctcagaga cagctgcccg gctcgagccc tgacctcatc    2100
tccacagcca tggctgcaga ctgctggaga agttctgagc ctgacaaggg ccaagctggt    2160
ccctggggct gttgccaggc tgacgcttat gaccccctgcc ttcagtgcag gccagaacag   2220
tatgggtcct tagacatacc ctctgctgag ccagtgggga ggagccctga cctttccaag    2280
tcaccagcac ataatcctct cttggaaaac gcccagagtt ctgagaaaac ggaagaaaat    2340
gaattcagcg gctgtaggtc tgagtcatcc ctcggcacct ctcatctcgg cacccctcca    2400
gcgctacctc gaaaaacaag gcctctgcag aagagtggag atgactcctc agaagaggaa    2460
gaaggggaag tagatagtga agttgaattt ccacgaagac agaggcccca tcgctgtatc    2520
agcagctgcc agtcatattc aacctttagc tctgagaatt tctctgtgtc tgatggagaa    2580
gagggaaata ccagtgacca ctcaaacagt cctgatgagt tagctgataa acttgaagac    2640
cgcttggcag agaagctaga cgacctgctg tcccagacgc cagagattcc cattgacata    2700
tcctcacact cggatgggct ctctgacaag gagtgtgccg tgcgccgtgt gaagactcag    2760
atgtctctgg gcaagctgtg tgtggaggaa cgtggctatg agaacccccat gcagtttgaa    2820 gaatcggact gtgactcttc agatggggag tgttctgatg ccacagttag gaccaataaa    2880
cactacagct ctgctacctg gtaatgaagg                                      2910

<210> SEQ ID NO 7
<211> LENGTH: 333
<212> TYPE: DNA
<213> ORGANISM: Homo sapiens

<400> SEQUENCE: 7
tacctataca tggagtattg tgcccatgga caactctacg aggtcttacg agctggcagg     60
aagatcacac ctcgattgct agtagactgg tccacaggaa ttgcaagtgg aatgaattat    120
ttgcacctcc ataaaattat tcatcgtgat ctcaaatcac ctaatgtttt agtgacccac    180
acagatgcgg taaaaatttc agattttggt acatctaagg aactcagtga caaaagtacc    240
aagatgtcat ttgctggcac ggtcgcatgg atggcgccag aggtgatacg gaatgaacct    300
gtctctgaaa aagttgatat ctggtctatg gta                                  333

<210> SEQ ID NO 8
<211> LENGTH: 859
<212> TYPE: PRT
<213> ORGANISM: Homo sapiens
```

<400> SEQUENCE: 8

```
Met Ala Cys Leu His Glu Thr Arg Thr Pro Ser Pro Ser Phe Gly Gly
  1               5                  10                  15

Phe Val Ser Thr Leu Ser Glu Ala Ser Met Arg Lys Leu Asp Pro Asp
             20                  25                  30

Thr Ser Asp Cys Thr Pro Glu Lys Asp Leu Thr Pro Thr His Val Leu
         35                  40                  45

Gln Leu His Glu Gln Asp Ala Gly Gly Pro Gly Ala Ala Gly Ser
 50                  55                  60

Pro Glu Ser Arg Ala Ser Arg Val Arg Ala Asp Glu Val Arg Leu Gln
 65                  70                  75                  80

Cys Gln Ser Gly Ser Gly Phe Leu Gly Leu Phe Gly Cys Leu Arg
                 85                  90                  95

Pro Val Trp Thr Met Ile Gly Lys Ala Tyr Ser Thr Glu His Lys Gln
             100                 105                 110

Gln Gln Glu Asp Leu Trp Glu Val Pro Phe Glu Glu Ile Leu Asp Leu
            115                 120                 125

Gln Trp Val Gly Ser Gly Ala Gln Gly Ala Val Phe Leu Gly Arg Phe
        130                 135                 140

His Gly Glu Glu Val Ala Val Lys Lys Val Arg Asp Leu Lys Glu Thr
145                 150                 155                 160

Asp Ile Lys His Leu Arg Lys Leu Lys His Pro Asn Ile Ile Thr Phe
                165                 170                 175

Lys Gly Val Cys Thr Gln Ala Pro Cys Tyr Cys Ile Leu Met Glu Phe
            180                 185                 190

Cys Ala Gln Gly Gln Leu Tyr Glu Val Leu Arg Ala Gly Arg Pro Val
        195                 200                 205

Thr Pro Ser Leu Leu Val Asp Trp Ser Met Gly Ile Ala Gly Gly Met
210                 215                 220

Asn Tyr Leu His Leu His Lys Ile Ile His Arg Asp Leu Lys Ser Pro
225                 230                 235                 240

Asn Met Leu Ile Thr Tyr Asp Asp Val Val Lys Ile Ser Asp Phe Gly
                245                 250                 255

Thr Ser Lys Glu Leu Ser Asp Lys Ser Thr Lys Met Ser Phe Ala Gly
            260                 265                 270

Thr Val Ala Trp Met Ala Pro Glu Val Ile Arg Asn Glu Pro Val Ser
        275                 280                 285

Glu Lys Val Asp Ile Trp Ser Phe Gly Val Val Leu Trp Glu Leu Leu
290                 295                 300

Thr Gly Glu Ile Pro Tyr Lys Asp Val Asp Ser Ser Ala Ile Ile Trp
305                 310                 315                 320

Gly Val Gly Ser Asn Ser Leu His Leu Pro Val Pro Ser Ser Cys Pro
                325                 330                 335

Asp Gly Phe Lys Ile Leu Leu Arg Gln Cys Trp Asn Ser Lys Pro Arg
            340                 345                 350

Asn Arg Pro Ser Phe Arg Gln Ile Leu Leu His Leu Asp Ile Ala Ser
        355                 360                 365

Ala Asp Val Leu Ser Thr Pro Gln Glu Thr Tyr Phe Lys Ser Gln Ala
370                 375                 380

Glu Trp Arg Glu Glu Val Lys Leu His Phe Glu Lys Ile Lys Ser Glu
385                 390                 395                 400

Gly Thr Cys Leu His Arg Leu Glu Glu Glu Leu Val Met Arg Arg Arg
                405                 410                 415
```

```
Glu Glu Leu Arg His Ala Leu Asp Ile Arg Glu His Tyr Glu Arg Lys
            420                 425                 430

Leu Glu Arg Ala Asn Asn Leu Tyr Met Glu Leu Asn Ala Leu Met Leu
            435                 440                 445

Gln Leu Glu Leu Lys Glu Arg Glu Leu Leu Arg Arg Glu Gln Ala Leu
            450                 455                 460

Glu Arg Arg Cys Pro Gly Leu Leu Lys Pro His Pro Ser Arg Gly Leu
465                 470                 475                 480

Leu His Gly Asn Thr Met Glu Lys Leu Ile Lys Lys Arg Asn Val Pro
                485                 490                 495

Gln Asn Leu Ser Pro His Ser Gln Arg Pro Asp Ile Leu Lys Ala Glu
                500                 505                 510

Ser Leu Leu Pro Lys Leu Asp Ala Ala Leu Ser Gly Val Gly Leu Pro
            515                 520                 525

Gly Cys Pro Lys Ala Pro Pro Ser Pro Gly Arg Ser Arg Arg Gly Lys
            530                 535                 540

Thr Arg His Arg Lys Ala Ser Ala Lys Gly Ser Cys Gly Asp Leu Pro
545                 550                 555                 560

Gly Leu Arg Thr Ala Val Pro Pro His Glu Pro Gly Gly Pro Gly Ser
                565                 570                 575

Pro Gly Gly Leu Gly Gly Gly Pro Ser Ala Trp Glu Ala Cys Pro Pro
                580                 585                 590

Ala Leu Arg Gly Leu His His Asp Leu Leu Leu Arg Lys Met Ser Ser
            595                 600                 605

Ser Ser Pro Asp Leu Leu Ser Ala Ala Leu Gly Ser Arg Gly Arg Gly
            610                 615                 620

Ala Thr Gly Gly Ala Gly Asp Pro Gly Ser Pro Pro Ala Arg Gly
625                 630                 635                 640

Asp Thr Pro Pro Ser Glu Gly Ser Ala Pro Gly Ser Thr Ser Pro Asp
                645                 650                 655

Ser Pro Gly Gly Ala Lys Gly Glu Pro Pro Pro Val Gly Pro Gly
                660                 665                 670

Glu Gly Val Gly Leu Leu Gly Thr Gly Arg Glu Gly Thr Ser Gly Arg
            675                 680                 685

Gly Gly Ser Arg Ala Gly Ser Gln His Leu Thr Pro Ala Ala Leu Leu
            690                 695                 700

Tyr Arg Ala Ala Val Thr Arg Ser Gln Lys Arg Gly Ile Ser Ser Glu
705                 710                 715                 720

Glu Glu Glu Gly Glu Val Asp Ser Glu Val Leu Thr Ser Ser Gln
                725                 730                 735

Arg Trp Pro Gln Ser Leu Asn Met Arg Gln Ser Leu Ser Thr Phe Ser
            740                 745                 750

Ser Glu Asn Pro Ser Asp Gly Glu Gly Thr Ala Ser Glu Pro Ser
            755                 760                 765

Pro Ser Gly Thr Pro Glu Val Gly Ser Thr Asn Thr Asp Glu Arg Pro
            770                 775                 780

Asp Glu Arg Ser Asp Asp Met Cys Ser Gln Gly Ser Glu Ile Pro Leu
785                 790                 795                 800

Asp Pro Pro Pro Ser Glu Val Ile Pro Gly Pro Glu Pro Ser Ser Leu
                805                 810                 815

Pro Ile Pro His Gln Glu Leu Leu Arg Glu Arg Gly Pro Pro Asn Ser
            820                 825                 830

Glu Asp Ser Asp Cys Asp Ser Thr Glu Leu Asp Asn Ser Asn Ser Val
            835                 840                 845
```

Asp Ala Leu Arg Pro Pro Ala Ser Leu Pro Pro
    850                 855

<210> SEQ ID NO 9
<211> LENGTH: 966
<212> TYPE: PRT
<213> ORGANISM: Homo sapiens

<400> SEQUENCE: 9

Met Ala Asn Phe Gln Glu His Leu Ser Cys Ser Ser Ser Pro His Leu
1               5                   10                  15

Pro Phe Ser Glu Ser Lys Thr Phe Asn Gly Leu Gln Asp Glu Leu Thr
            20                  25                  30

Ala Met Gly Asn His Pro Ser Pro Lys Leu Leu Glu Asp Gln Gln Glu
        35                  40                  45

Lys Gly Met Val Arg Thr Glu Leu Ile Glu Ser Val His Ser Pro Val
50                  55                  60

Thr Thr Thr Val Leu Thr Ser Val Ser Glu Asp Ser Arg Asp Gln Phe
65                  70                  75                  80

Glu Asn Ser Val Leu Gln Leu Arg Glu His Asp Glu Ser Glu Thr Ala
                85                  90                  95

Val Ser Gln Gly Asn Ser Asn Thr Val Asp Gly Glu Ser Thr Ser Gly
            100                 105                 110

Thr Glu Asp Ile Lys Ile Gln Phe Ser Arg Ser Gly Ser Gly Ser Gly
        115                 120                 125

Gly Phe Leu Glu Gly Leu Phe Gly Cys Leu Arg Pro Val Trp Asn Ile
    130                 135                 140

Ile Gly Lys Ala Tyr Ser Thr Asp Tyr Lys Leu Gln Gln Gln Asp Thr
145                 150                 155                 160

Trp Glu Val Pro Phe Glu Glu Ile Ser Glu Leu Gln Trp Leu Gly Ser
                165                 170                 175

Gly Ala Gln Gly Ala Val Phe Leu Gly Lys Phe Arg Ala Glu Glu Val
            180                 185                 190

Ala Ile Lys Lys Val Arg Glu Gln Asn Glu Thr Asp Ile Lys His Leu
        195                 200                 205

Arg Lys Leu Lys His Pro Asn Ile Ile Ala Phe Lys Gly Val Cys Thr
    210                 215                 220

Gln Ala Pro Cys Tyr Cys Ile Ile Met Glu Tyr Cys Ala His Gly Gln
225                 230                 235                 240

Leu Tyr Glu Val Leu Arg Ala Gly Arg Lys Ile Thr Pro Arg Leu Leu
                245                 250                 255

Val Asp Trp Ser Thr Gly Ile Ala Ser Gly Met Asn Tyr Leu His Leu
            260                 265                 270

His Lys Ile Ile His Arg Asp Leu Lys Ser Pro Asn Val Leu Val Thr
        275                 280                 285

His Thr Asp Ala Val Lys Ile Ser Asp Phe Gly Thr Ser Lys Glu Leu
    290                 295                 300

Ser Asp Lys Ser Thr Lys Met Ser Phe Ala Gly Thr Val Ala Trp Met
305                 310                 315                 320

Ala Pro Glu Val Ile Arg Asn Glu Pro Val Ser Glu Lys Val Asp Ile
                325                 330                 335

Trp Ser Phe Gly Val Val Leu Trp Glu Leu Leu Thr Gly Glu Ile Pro
            340                 345                 350

Tyr Lys Asp Val Asp Ser Ser Ala Ile Ile Trp Gly Val Gly Ser Asn
        355                 360                 365

```
Ser Leu His Leu Pro Val Pro Ser Thr Cys Pro Asp Gly Phe Lys Ile
    370                 375                 380

Leu Met Lys Gln Thr Trp Gln Ser Lys Pro Arg Asn Arg Pro Ser Phe
385                     390                 395                 400

Arg Gln Thr Leu Met His Leu Asp Ile Ala Ser Ala Asp Val Leu Ala
                405                 410                 415

Thr Pro Gln Glu Thr Tyr Phe Lys Ser Gln Ala Glu Trp Arg Glu Glu
            420                 425                 430

Val Lys Lys His Phe Glu Lys Ile Lys Ser Glu Gly Thr Cys Ile His
        435                 440                 445

Arg Leu Asp Glu Glu Leu Ile Arg Arg Arg Glu Glu Leu Arg His
    450                 455                 460

Ala Leu Asp Ile Arg Glu His Tyr Glu Arg Lys Leu Glu Arg Ala Asn
465                 470                 475                 480

Asn Leu Tyr Met Glu Leu Ser Ala Ile Met Leu Gln Leu Glu Met Arg
                485                 490                 495

Glu Lys Glu Leu Ile Lys Arg Glu Gln Ala Val Glu Lys Lys Tyr Pro
            500                 505                 510

Gly Thr Tyr Lys Arg His Pro Val Arg Pro Ile Ile His Pro Asn Ala
        515                 520                 525

Met Glu Lys Leu Met Lys Arg Lys Gly Val Pro His Lys Ser Gly Met
530                 535                 540

Gln Thr Lys Arg Pro Asp Leu Leu Arg Ser Glu Gly Ile Pro Thr Thr
545                 550                 555                 560

Glu Val Ala Pro Thr Ala Ser Pro Leu Ser Gly Ser Pro Lys Met Ser
                565                 570                 575

Thr Ser Ser Ser Lys Ser Arg Tyr Arg Ser Lys Pro Arg His Arg Arg
            580                 585                 590

Gly Asn Ser Arg Gly Ser His Ser Asp Phe Ala Ala Ile Leu Lys Asn
        595                 600                 605

Gln Pro Ala Gln Glu Asn Ser Pro His Pro Thr Tyr Leu His Gln Ala
    610                 615                 620

Gln Ser Gln Tyr Pro Ser Leu His His His Asn Ser Leu Gln Gln Gln
625                 630                 635                 640

Tyr Gln Gln Pro Pro Ala Met Ser Gln Ser His His Pro Arg Leu
                645                 650                 655

Asn Met His Gly Gln Asp Ile Ala Thr Cys Ala Asn Asn Leu Arg Tyr
            660                 665                 670

Phe Gly Pro Ala Ala Ala Leu Arg Ser Pro Leu Ser Asn His Ala Gln
        675                 680                 685

Arg Gln Leu Pro Gly Ser Ser Pro Asp Leu Ile Ser Thr Ala Met Ala
    690                 695                 700

Ala Asp Cys Trp Arg Ser Ser Glu Pro Asp Lys Gly Gln Ala Gly Pro
705                 710                 715                 720

Trp Gly Cys Cys Gln Ala Asp Ala Tyr Asp Pro Cys Leu Gln Cys Arg
                725                 730                 735

Pro Glu Gln Tyr Gly Ser Leu Asp Ile Pro Ser Ala Glu Pro Val Gly
            740                 745                 750

Arg Ser Pro Asp Leu Ser Lys Ser Pro Ala His Asn Pro Leu Leu Glu
        755                 760                 765

Asn Ala Gln Ser Ser Glu Lys Thr Glu Glu Asn Glu Phe Ser Gly Cys
    770                 775                 780

Arg Ser Glu Ser Ser Leu Gly Thr Ser His Leu Gly Thr Pro Pro Ala
```

-continued

```
            785                 790                 795                 800
Leu Pro Arg Lys Thr Arg Pro Leu Gln Lys Ser Gly Asp Asp Ser Ser
                805                 810                 815

Glu Glu Glu Glu Gly Glu Val Asp Ser Glu Val Glu Phe Pro Arg Arg
            820                 825                 830

Gln Arg Pro His Arg Cys Ile Ser Ser Cys Gln Ser Tyr Ser Thr Phe
            835                 840                 845

Ser Ser Glu Asn Phe Ser Val Ser Asp Gly Glu Gly Asn Thr Ser
    850                 855                 860

Asp His Ser Asn Ser Pro Asp Glu Leu Ala Asp Lys Leu Glu Asp Arg
865                 870                 875                 880

Leu Ala Glu Lys Leu Asp Asp Leu Leu Ser Gln Thr Pro Glu Ile Pro
                885                 890                 895

Ile Asp Ile Ser Ser His Ser Asp Gly Leu Ser Asp Lys Glu Cys Ala
            900                 905                 910

Val Arg Arg Val Lys Thr Gln Met Ser Leu Gly Lys Leu Cys Val Glu
            915                 920                 925

Glu Arg Gly Tyr Glu Asn Pro Met Gln Phe Glu Glu Ser Asp Cys Asp
    930                 935                 940

Ser Ser Asp Gly Glu Cys Ser Asp Ala Thr Val Arg Thr Asn Lys His
945                 950                 955                 960

Tyr Ser Ser Ala Thr Trp
                965
```